United States Patent
Kobayashi

(10) Patent No.: US 9,517,011 B2
(45) Date of Patent: Dec. 13, 2016

(54) INFORMATION PROCESSING APPARATUS, PORTABLE COMMUNICATION TERMINAL, AND CONTROL METHODS AND CONTROL PROGRAMS THEREOF

(71) Applicant: NEC Corporation, Tokyo (JP)

(72) Inventor: Yoshikazu Kobayashi, Tokyo (JP)

(73) Assignee: NEC Corporation, Tokyo (JP)

( * ) Notice: Subject to any disclaimer, the term of this patent is extended or adjusted under 35 U.S.C. 154(b) by 78 days.

(21) Appl. No.: 14/403,718

(22) PCT Filed: May 22, 2013

(86) PCT No.: PCT/JP2013/064234
§ 371 (c)(1),
(2) Date: Nov. 25, 2014

(87) PCT Pub. No.: WO2013/179981
PCT Pub. Date: Dec. 5, 2013

(65) Prior Publication Data
US 2015/0208921 A1 Jul. 30, 2015

(30) Foreign Application Priority Data
May 30, 2012 (JP) ................................. 2012-123801

(51) Int. Cl.
G08C 19/22 (2006.01)
A61B 5/00 (2006.01)
G06Q 50/24 (2012.01)
A61B 5/01 (2006.01)
A61B 5/021 (2006.01)
A61B 5/024 (2006.01)
H04W 88/04 (2009.01)

(52) U.S. Cl.
CPC ............... *A61B 5/0022* (2013.01); *A61B 5/01* (2013.01); *A61B 5/021* (2013.01); *A61B 5/024* (2013.01);
(Continued)

(58) Field of Classification Search
CPC ..... A61B 5/0022; A61B 5/7465; A61B 5/024; A61B 5/021; A61B 5/742; A61B 5/01; G06F 13/00; H04W 88/04; G06Q 50/24
(Continued)

(56) References Cited

U.S. PATENT DOCUMENTS 8,185,623 B2 *  5/2012  Lewis ................... G06F 19/322
                                                        340/539.12
2009/0292995 A1 * 11/2009  Anne .................... H04L 12/413
                                                        715/736
(Continued)

FOREIGN PATENT DOCUMENTS

JP     2004-147705 A     5/2004
JP     2005-245956 A     9/2005
(Continued)

OTHER PUBLICATIONS

International Search Report corresponding to PCT/JP2013/064234, dated Jul. 16, 2013 (5 pages).
(Continued)

*Primary Examiner* — Dhaval Patel
(74) *Attorney, Agent, or Firm* — Wilmer Cutler Pickering Hale and Dorr LLP

(57) ABSTRACT

An information processing apparatus includes an acquisition unit that, when a medical measurement device is connected to a portable communication terminal, acquires specifying information for specifying the medical measurement device via the portable communication terminal, a first receiver that receives, via the portable communication terminal, measurement result information of a measurement target person measured by the medical measurement device by executing a driver program corresponding to the specifying information, a second receiver that receives, from the portable communication terminal, measurement target person infor-
(Continued)

mation for specifying the measurement target person measured by the medical measurement device, an accumulator that accumulates the measurement target person information and the measurement result information in association with each other, and a transmitter that transmits accumulated information to one of the portable communication terminal and a medical care worker communication terminal.

14 Claims, 28 Drawing Sheets

(52) U.S. Cl.
CPC .............. *A61B 5/742* (2013.01); *A61B 5/7465* (2013.01); *G06Q 50/24* (2013.01); *H04W 88/04* (2013.01)

(58) Field of Classification Search
USPC ........... 340/870.07, 5.1, 572.1, 539.12, 5.61, 340/573.1, 687; 709/217, 219, 203, 224; 705/2, 705/3
See application file for complete search history.

(56) References Cited

U.S. PATENT DOCUMENTS

| | | | |
|---|---|---|---|
| 2011/0074585 A1* | 3/2011 | Harmon | G06F 19/327 340/573.1 |
| 2011/0320131 A1* | 12/2011 | Hibino | G06F 19/3418 702/19 |
| 2012/0029303 A1* | 2/2012 | Shaya | A61B 5/0022 600/300 |
| 2012/0041785 A1* | 2/2012 | Tsunomori | A61B 6/5235 705/3 |
| 2012/0226768 A1* | 9/2012 | Gaines | G06F 19/3418 709/217 |
| 2012/0233679 A1* | 9/2012 | Shedrinsky | G06F 19/327 726/7 |
| 2013/0211265 A1 | 8/2013 | Bedingham et al. | |

FOREIGN PATENT DOCUMENTS

| | | |
|---|---|---|
| JP | 2007-080094 A | 3/2007 |
| JP | 2007-102308 A | 4/2007 |
| JP | 2007-193429 A | 8/2007 |
| JP | 2008-016906 A | 1/2008 |
| JP | 2010-176471 A | 8/2010 |
| JP | 2011-172068 A | 9/2011 |
| WO | WO-2008/030249 | 3/2008 |
| WO | WO-2012/054268 A2 | 4/2012 |

OTHER PUBLICATIONS

Extended European Search Report corresponding to European Application No. 13796487.0, dated Oct. 22, 2015, 6 pages.
Japanese Office Action issued by the Japan Patent Office for Application No. 2012-123801 dated Sep. 27, 2016 (4 pages).

* cited by examiner

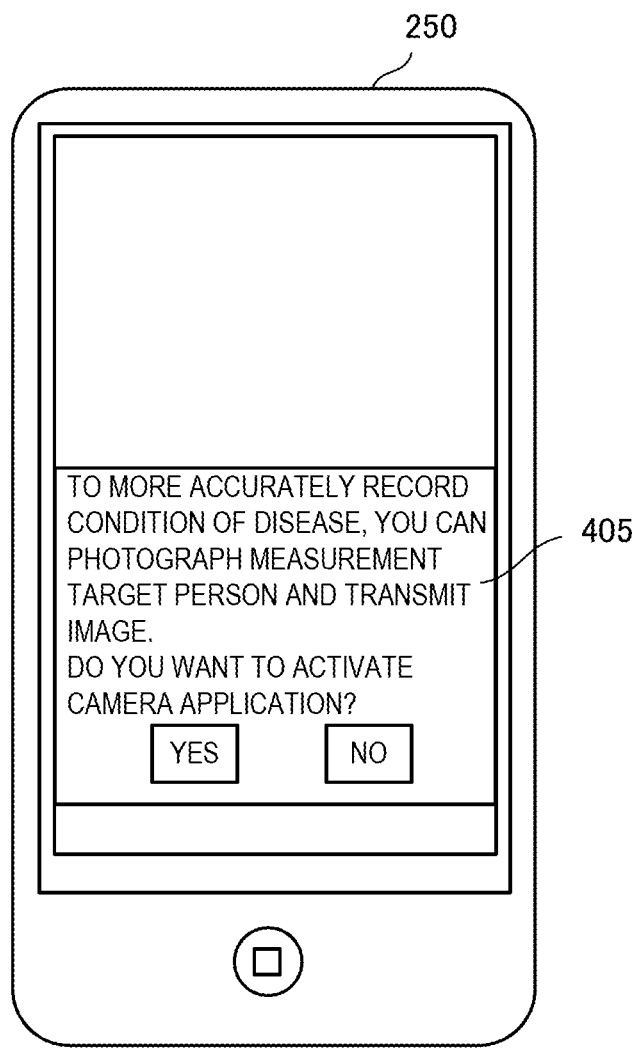
F I G. 4E

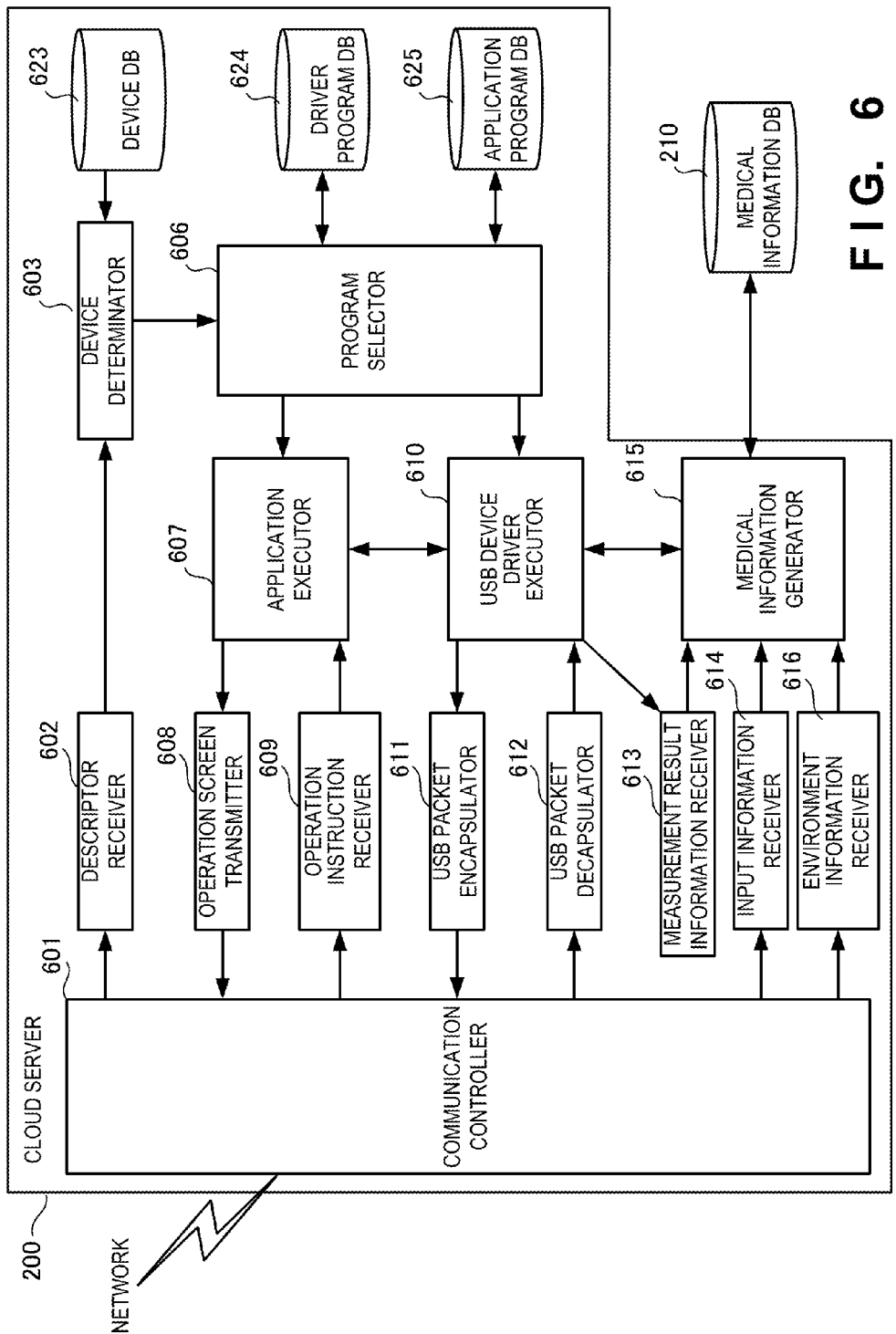

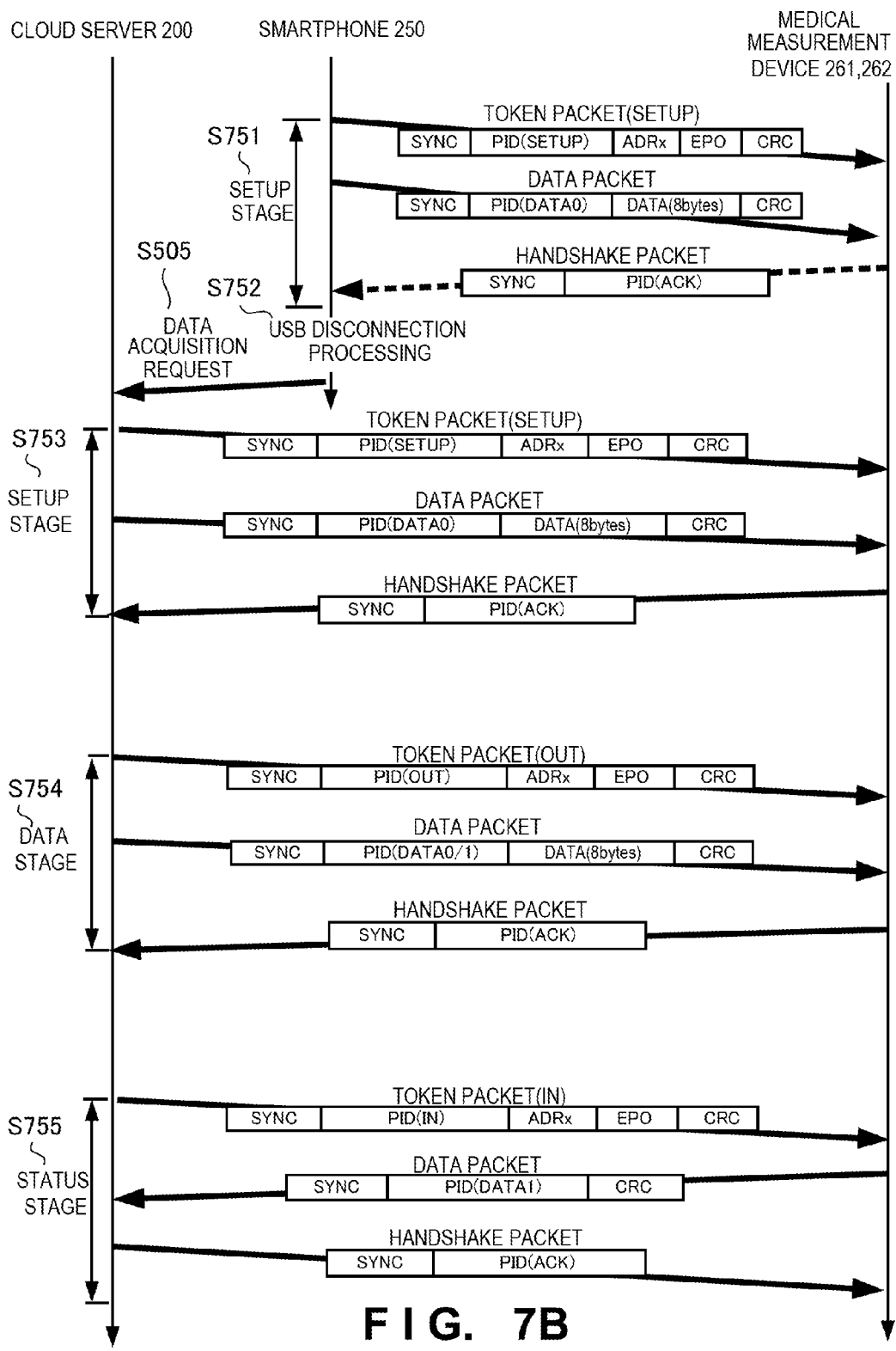
F I G. 7B

| DEVICE DESCRIPTOR | INTERFACE DESCRIPTOR | VENDOR ID | PRODUCT ID |
|---|---|---|---|
| AAAAAA | XXXXXX | ○○○○ | ●●●● |
| BBBBBB | YYYYY | △△△△ | ▲▲▲▲ |
| CCCCCC | ZZZZZZ | □□□□ | ■■■■ |
| ... | ... | ... | ... |

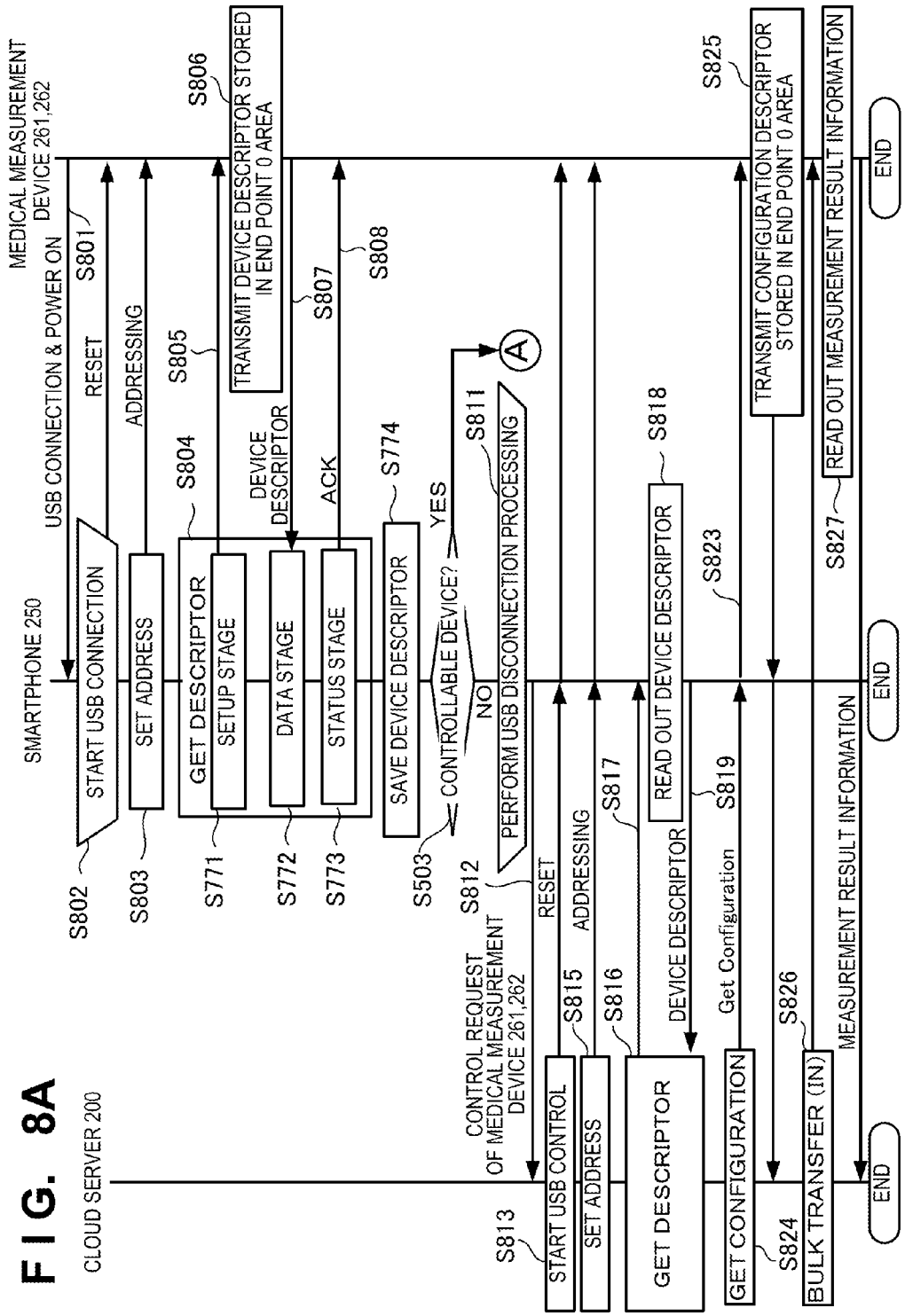

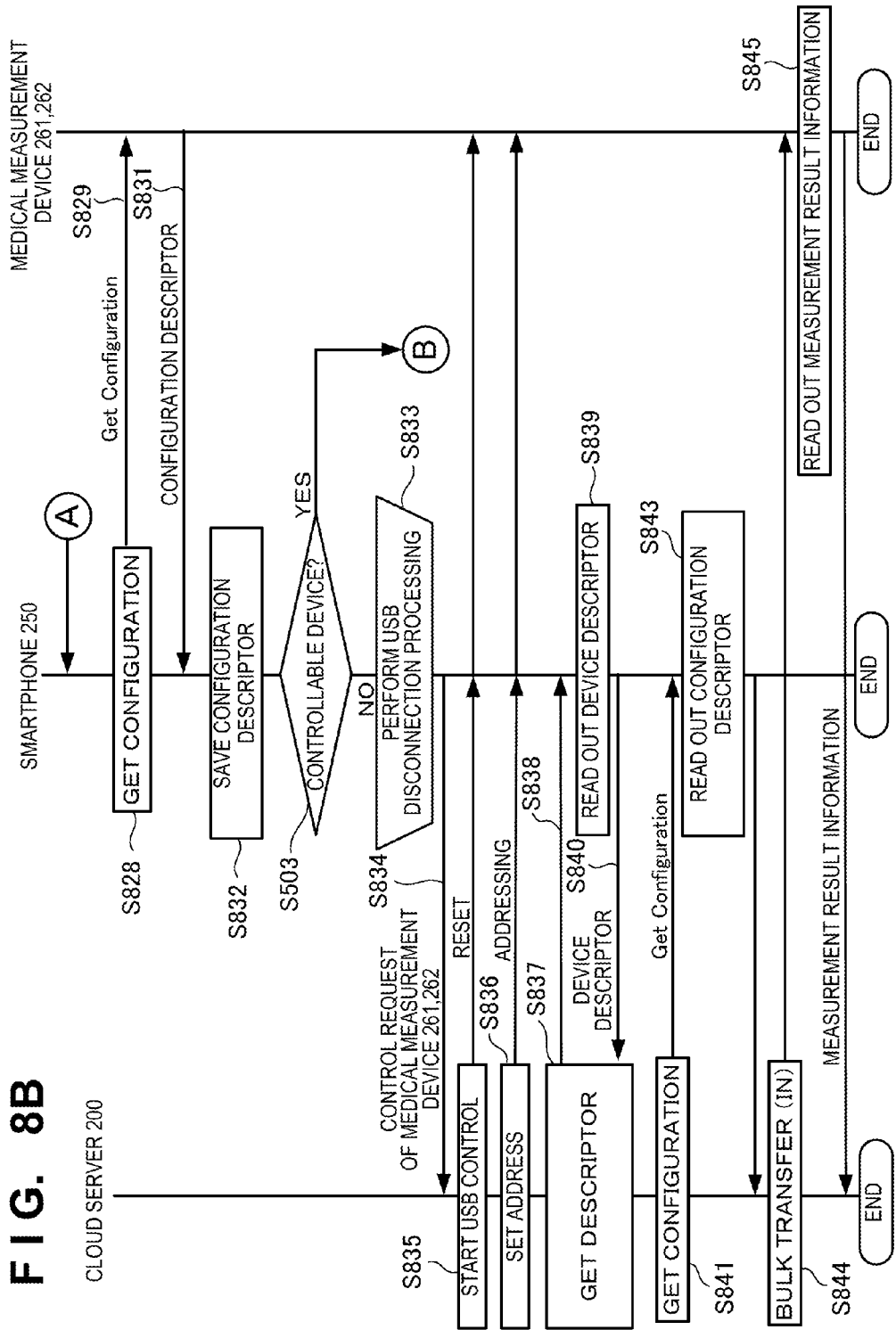

1200

| MAIN USER | |
|---|---|
| USER ID : | ... |
| INDIVIDUAL NUMBER OF SMARTPHONE | ... |
| NAME : | ... |
| ADDRESS : | ... |
| TELEPHONE NUMBER : | ... |
| MAIL ADDRESS : | ... |
| AGE : | ... |
| SEX : | ... |
| MEDICAL HISTORY : | ... |
| CHRONICAL DISEASE : | |
| | ... |
| FAMILY MAKEUP 1 | ... |
| USER ID : | ... |
| RELATION : | ... |
| NAME : | ... |
| AGE : | ... |
| SEX : | ... |
| MEDICAL HISTORY : | |
| ⋮ | ⋮ |

F I G. 12

INFORMATION PROCESSING APPARATUS, PORTABLE COMMUNICATION TERMINAL, AND CONTROL METHODS AND CONTROL PROGRAMS THEREOF

CROSS-REFERENCE TO RELATED APPLICATIONS

This application is a national stage application of International Application No. PCT/JP2013/064234 entitled "INFORMATION PROCESSING APPARATUS, PORTABLE COMMUNICATION TERMINAL, AND CONTROL METHODS AND CONTROL PROGRAMS THEREOF," filed on May 22, 2013, which claims the benefit of the priority of Japanese Patent Application No. 2012-123801, filed on May 30, 2012, the disclosures of each of which are hereby incorporated by reference in their entirety.

TECHNICAL FIELD

The present invention relates to an information processing apparatus used for medical care, a portable communication terminal, and control methods and control programs thereof.

BACKGROUND ART

In the above technical field, paragraph 0063 of patent literature 1 discloses a technique of operating, from a virtual PC, a USB device inserted in a client terminal. Patent literature 2 discloses a technique of activating a surgical operating system from a portable terminal. Patent literature 3 discloses a medical knowledge database.

CITATION LIST

Patent Literature

Patent literature 1: Japanese Patent Laid-Open No. 2007-193429
Patent literature 2: Japanese Patent Laid-Open No. 2007-080094
Patent literature 3: WO 2008/030249

SUMMARY OF THE INVENTION

Technical Problem

In the techniques described in the above literatures, however, data of a sphygmomanometer, a blood glucose sensor, a heart rate monitor, or the like is transmitted to a server by an operation of using a dedicated communication module, an operation of storing the data and bringing it to a hospital, or an operation of directly inputting the data to a PC.

The conventional techniques cannot cope with a current situation in which cooperation between a doctor and a medical device used by an individual other than a doctor is indispensable along with the development of a medical measurement device independently used at home such as a sphygmomanometer, and popularization of same-day medical care and home medical care.

As drivers and applications for medical sensors, there are drivers and applications created for a PC. However, it is inefficient to develop again such a driver and application for each smart device. This makes it difficult to use a portable communication terminal such as a smartphone or a tablet to control a medical device, and the user friendliness is poor.

The present invention enables to provide a technique of solving the above-described problem.

Solution to Problem

One aspect of the present invention provides an information processing apparatus comprising:

an acquisition unit that, when a medical measurement device is connected to a portable communication terminal, acquires specifying information for specifying the medical measurement device via the portable communication terminal;

a first receiver that receives, via the portable communication terminal, measurement result information of a measurement target person measured by the medical measurement device by executing a driver program corresponding to the specifying information;

a second receiver that receives, from the portable communication terminal, measurement target person information for specifying the measurement target person measured by the medical measurement device;

an accumulator that accumulates the measurement target person information and the measurement result information in association with each other; and a transmitter that transmits accumulated information to one of the portable communication terminal and a medical care worker communication terminal.

Another aspect of the present invention provides a method comprising:

when a medical measurement device is connected to a portable communication terminal, acquiring specifying information for specifying the medical measurement device via the portable communication terminal;

receiving, via the portable communication terminal, measurement result information of a measurement target person measured by the medical measurement device by executing a driver program corresponding to the specifying information;

receiving, from the portable communication terminal, measurement target person information for specifying the measurement target person measured by the medical measurement device;

accumulating the measurement target person information and the measurement result information in association with each other; and transmitting accumulated information to one of the portable communication terminal and a medical care worker communication terminal.

Still other aspect of the present invention provides a program for causing a computer to execute a method, comprising:

when a medical measurement device is connected to a portable communication terminal, acquiring specifying information for specifying the medical measurement device via the portable communication terminal;

receiving, via the portable communication terminal, measurement result information of a measurement target person measured by the medical measurement device by executing a driver program corresponding to the specifying information;

receiving, from the portable communication terminal, measurement target person information for specifying the measurement target person measured by the medical measurement device;

accumulating the measurement target person information and the measurement result information in association with each other; and transmitting accumulated information to one of the portable communication terminal and a medical care worker communication terminal.

Still other aspect of the present invention provides a portable communication terminal comprising:

a determinator that determines, when a medical measurement device is connected via a communication interface, whether a local terminal can control the medical measurement device;

a request unit that, when the determinator determines that the local terminal cannot control the medical measurement device, accesses a server via a wireless communication network, and requests acquisition of measurement result information from the medical measurement device;

a signal transfer control unit that controls signal transfer between the medical measurement device and the server via the communication interface and the wireless communication network so as to be able to establish communication between the medical measurement device and the server and acquire, by the server, measurement result information measured by the medical measurement device; and a transmitter that transmits, to the server in association with each other, the measurement result information and measurement target person information for specifying a measurement target person.

Still other aspect of the present invention provides a control method of a portable communication terminal, comprising:

determining, when a medical measurement device is connected via a communication interface, whether a local terminal can control the medical measurement device;

when the local terminal is determined in the determining not to be able to control the medical measurement device, accessing a server via a wireless communication network, and requesting acquisition of measurement result information from the medical measurement device;

controlling signal transfer between the medical measurement device and the server via the communication interface and the wireless communication network so as to be able to establish communication between the medical measurement device and the server and acquire, by the server, measurement result information measured by the medical measurement device; and transmitting, to the server in association with each other, the measurement result information and measurement target person information for specifying a measurement target person.

Still other aspect of the present invention provides a control program of a portable communication terminal for causing a computer to execute a method, comprising:

determining, when a medical measurement device is connected via a communication interface, whether a local terminal can control the medical measurement device;

when the local terminal is determined in the determining not to be able to control the medical measurement device, accessing a server via a wireless communication network, and requesting acquisition of measurement result information from the medical measurement device;

controlling signal transfer between the medical measurement device and the server via the communication interface and the wireless communication network so as to be able to establish communication between the medical measurement device and the server and acquire, by the server, measurement result information measured by the medical measurement device; and transmitting, to the server in association with each other, the measurement result information and measurement target person information for specifying a measurement target person.

Advantageous Effects of Invention

According to the present invention, medical data can be collected by only connecting a handy portable communication terminal to a medical measurement device.

BRIEF DESCRIPTION OF DRAWINGS

FIG. 4E is a view showing an example of a display screen displayed on the smartphone in the second embodiment of the present invention;

FIG. 6 is a block diagram showing the functional arrangement of a cloud server in the second embodiment of the present invention;

FIG. 7B is a chart showing an example of packet transmission/reception processing in the information processing system according to the second embodiment of the present invention;

FIG. 7E is a table showing the structure of a device database used in the information processing system according to the second embodiment of the present invention;

FIG. 8A is a chart showing an example of communication establishment processing between a server and a device in the information processing system according to the second embodiment of the present invention;

FIG. 8B is a chart showing the example of communication establishment processing between the server and the device in the information processing system according to the second embodiment of the present invention;

FIG. 12 is a view showing the structure of a personal information database in the second embodiment of the present invention.

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise. In this specification, a "medical care worker" mainly indicates a doctor. However, the scope of rights of the present invention is not limited to this, and the "medical care worker" includes persons with medical knowledge such as a nurse, a pharmacist, a physical therapist, an occupational therapist, and a care worker.

[First Embodiment]

Figure 1:
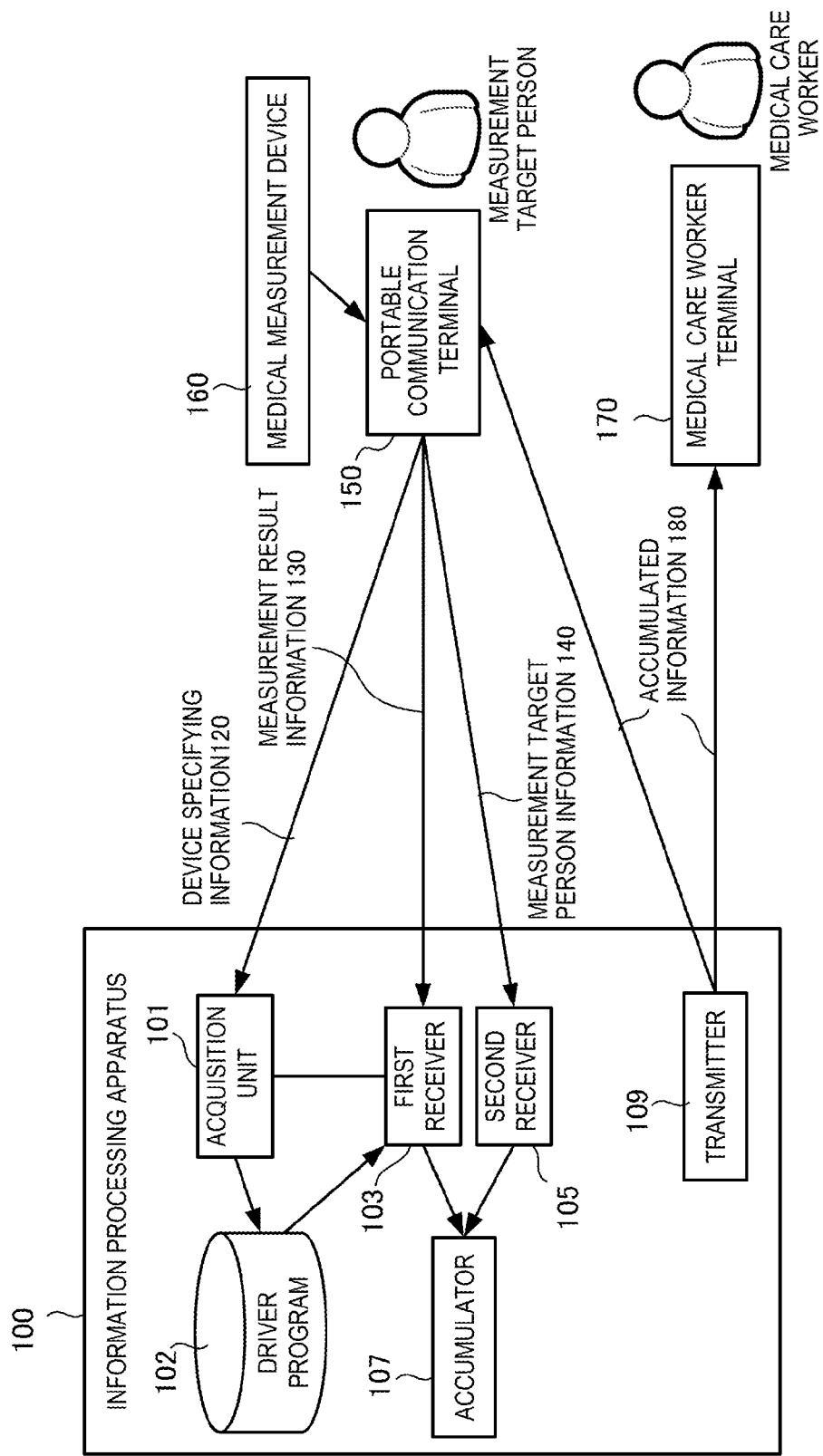
FIG. 1 is a block diagram showing the arrangement of an information processing system according to the first embodiment of the present invention.

An information processing apparatus 100 according to the first embodiment of the present invention will be described with reference to FIG. 1. The information processing apparatus 100 collects and accumulates data provided by a medical measurement device 160 connected to a portable communication terminal 150.

The information processing apparatus 100 can communicate with the portable communication terminal 150 used by an individual, and a medical care worker terminal 170 used by a medical care worker. The information processing apparatus 100 includes an acquisition unit 101, a first receiver 103, a second receiver 105, an accumulator 107, and a transmitter 109.

When the medical measurement device 160 is connected to the portable communication terminal 150, the acquisition unit 101 acquires, via the portable communication terminal 150, device specifying information 120 for specifying the medical measurement device 160.

By executing a driver program 102 corresponding to the device specifying information 120, the first receiver 103 receives, via the portable communication terminal 150, measurement result information 130 of a measurement target person measured by the medical measurement device 160.

The second receiver 105 receives, from the portable communication terminal 150, measurement target person information 140 for specifying the measurement target person measured by the medical measurement device 160.

The accumulator 107 accumulates the measurement target person information 140 and the measurement result information 130 in association with each other.

The transmitter 109 transmits accumulated information 180 to the portable communication terminal 150 or the medical care worker terminal 170.

With the above arrangement, medical data can be collected by only connecting a handy portable communication terminal to a medical measurement device.

[Second Embodiment]

Figure 2:
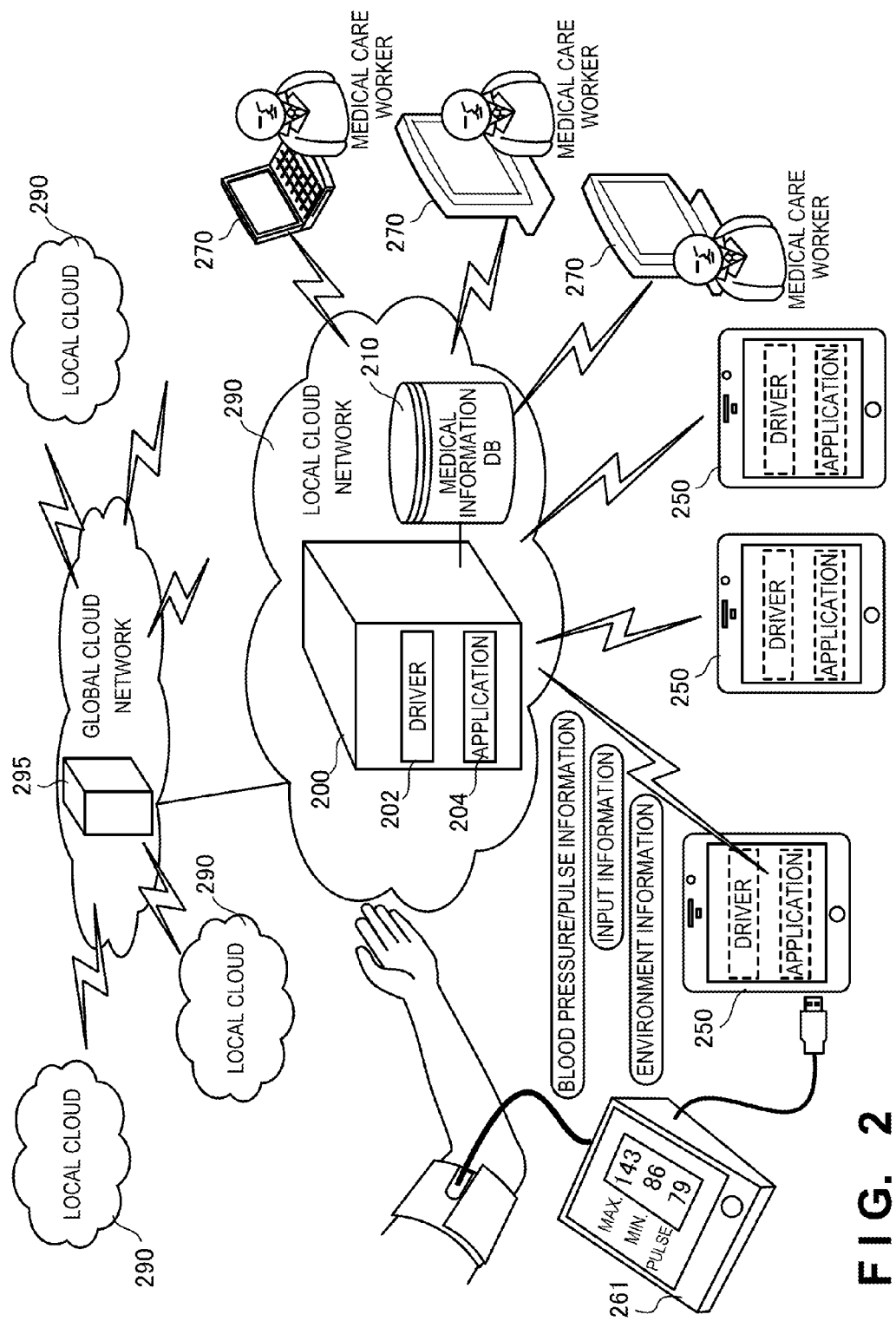
FIG. 2 is a view showing an example of the use of an information processing system according to the second embodiment of the present invention.
Figure 3:
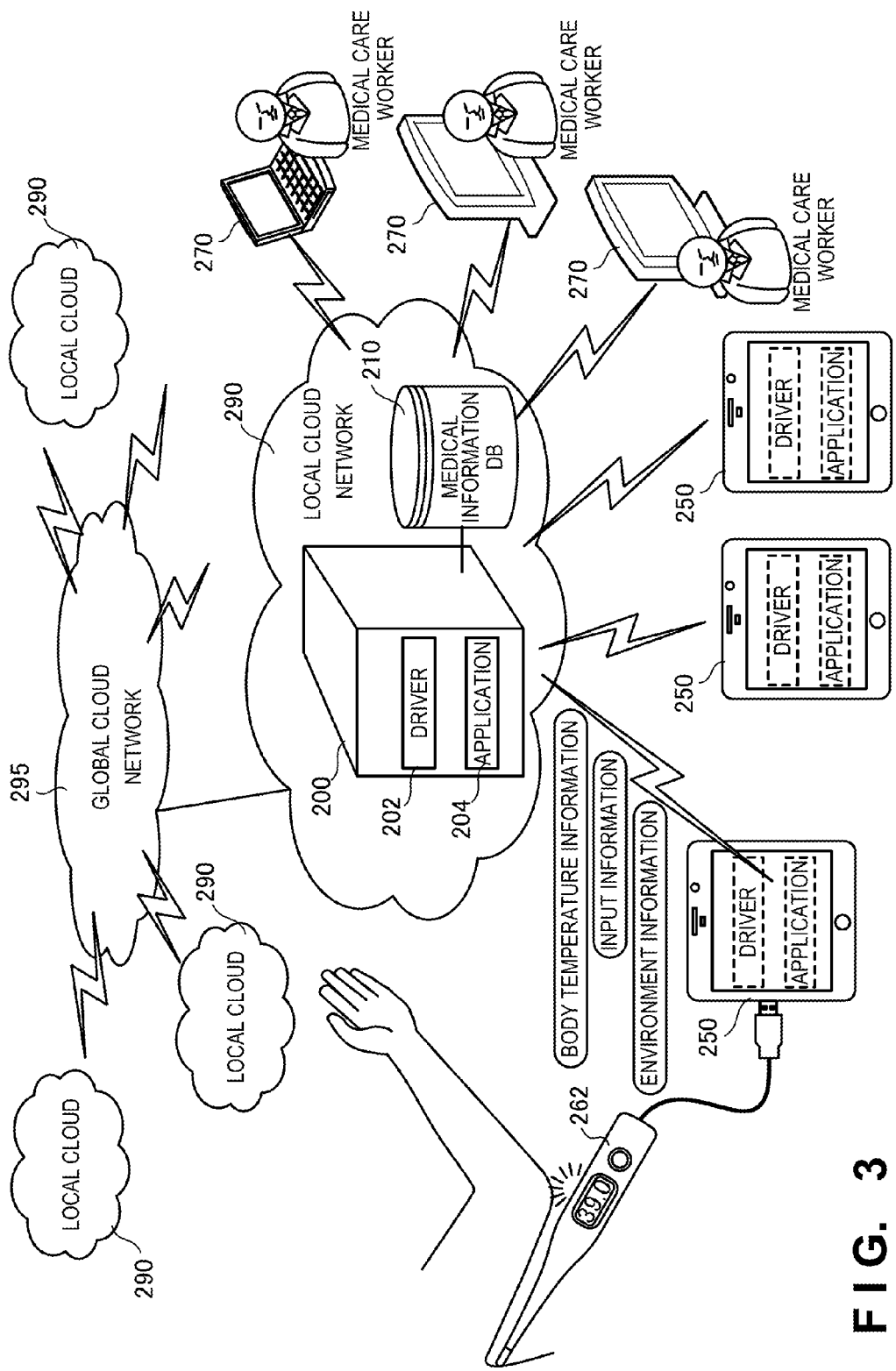
FIG. 3 is a view showing another example of the use of the information processing system according to the second embodiment of the present invention.

A cloud server 200 as an information processing apparatus according to the second embodiment of the present invention will be described next with reference to FIGS. 2, 3, and 4. FIGS. 2 and 3 are views for explaining an information processing system including the cloud server 200 and the use method of the information processing system.

(Overall System Arrangement and Processing Sequence)

Referring to FIG. 2, the cloud server 200 is connected to a medical information database (medical information DB) 210 to constitute a local cloud network 290. The cloud server 200 can communicate with a plurality of smartphones 250, which are an example of a portable communication terminal, via a wireless communication network. The wireless communication network may be a mobile phone communication network or a network using a wireless communication interface (for example, wireless communication standard IEEE802.11 series (IEEE802.11a, b, c, d, e)).

Referring to FIG. 2, one smartphone 250 is connected to a blood pressure/pulse measurement device 261, which is an example of a medical measurement device, via a USB (Universal Serial Bus) interface. Referring to FIG. 3, one smartphone 250 is connected to a body temperature measurement device 262, which is another example of the medical measurement device, via a USB interface. Note that the USB interface is used as an example of a communication interface. However, the present invention is not limited to this, and the communication interface may be another data communication interface (for example, a serial communication interface, IEEE1394, or HDMI®).

Figure 4A:
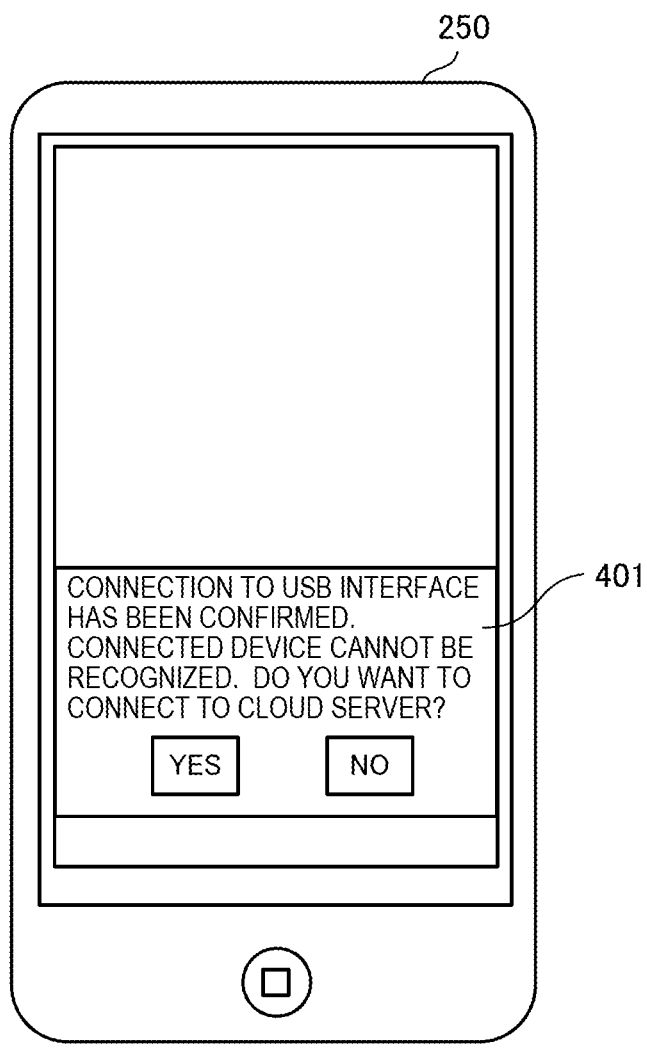
FIG. 4A is a view showing an example of a display screen displayed on a smartphone in the second embodiment of the present invention.

When the smartphone 250 is connected to the medical measurement device 261 or 262, it first determines whether it includes a driver program specialized in the medical measurement device 261 or 262. If the smartphone 250 determines that the local terminal includes the driver program, it receives measurement information from the medical measurement device 261 or 262 by using the driver program. There are various kinds of medical measurement devices. Thus, if driver programs corresponding to respective devices are stored in the smartphone 250, they waste the storage capacity of the smartphone 250. Normally, a screen 401 shown in FIG. 4A is displayed on the smartphone 250 to prompt the user to make a confirmation without storing such a driver program in the smartphone 250. When the user requests a connection to the cloud server 200, the smartphone 250 requests the cloud server 200 to establish communication with the medical measurement device 261 or 262 and acquire a measurement value.

When the cloud server 200 establishes communication with the medical measurement device 261 or 262 via the smartphone 250, it receives measurement result information (for example, blood pressure/pulse information or body temperature information) from the medical measurement device 261 or 262. The cloud server 200 stores the received measurement result information in the medical information database 210.

The cloud server 200 activates an application program 204 corresponding to the type of the medical measurement device 261 or 262, and displays various GUIs (Graphic User Interfaces) on the display of the smartphone 250. The application program 204 acts as if it were installed in the smartphone 250. The application program 204 detects a user operation to the smartphone 250, performs processing corresponding to this operation, and changes the screen display of the smartphone 250. This has an advantage in which the storage capacity of the smartphone 250 is not wasted and a version upgrade of the application need not be performed on the user side.

Figure 4B:
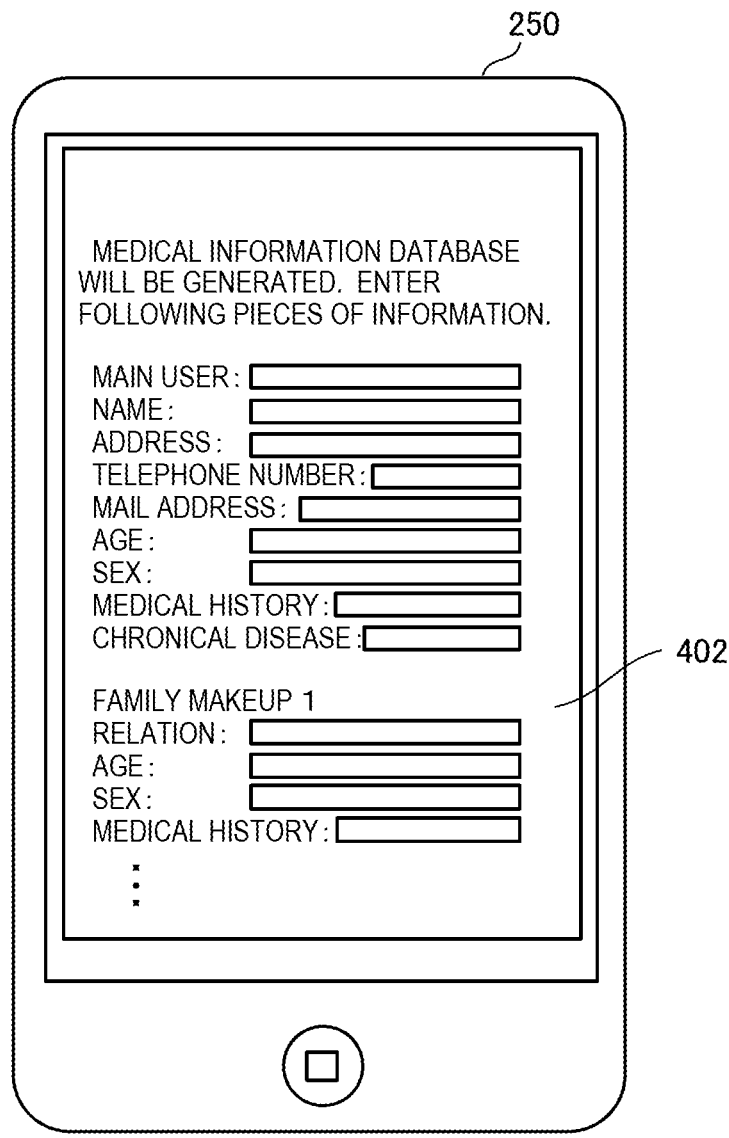
FIG. 4B is a view showing an example of a display screen displayed on the smartphone in the second embodiment of the present invention.
Figure 4C:
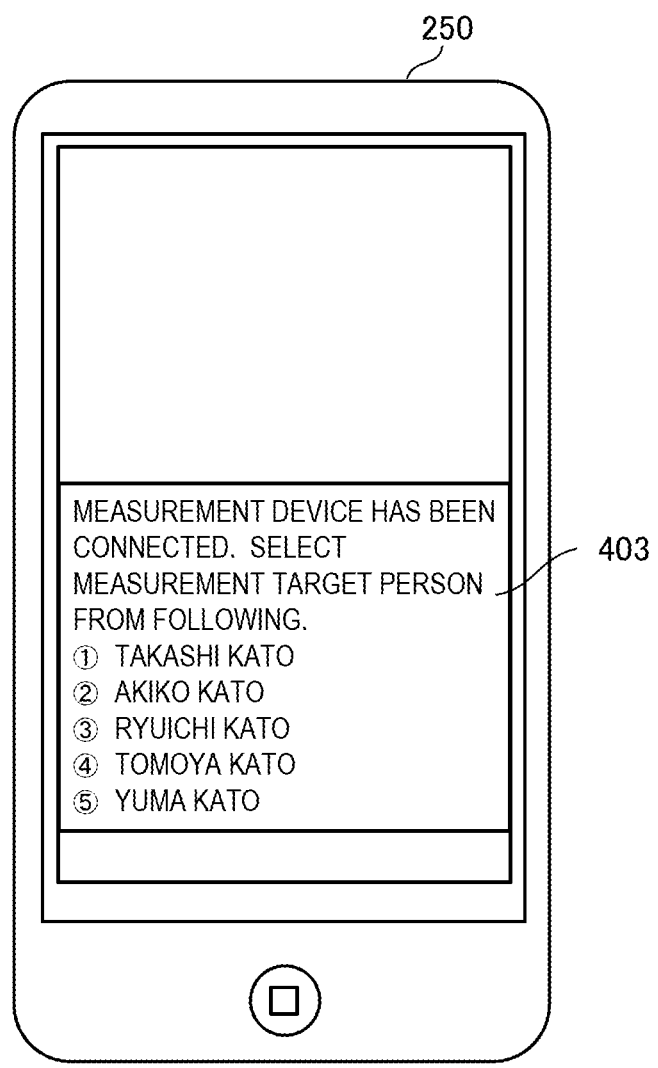
FIG. 4C is a view showing an example of a display screen displayed on the smartphone in the second embodiment of the present invention.

The application program 204 confirms individual information of the smartphone 250, and determines whether the smartphone 250 has measured and acquired medical information for the first time. If the application program 204 determines that the smartphone 250 has measured and acquired medical information for the first time, it prompts a user to input, via a GUI, information about the user (for example, an owner or his family) who will be a measurement target person. The application program 204 registers the input information as part of medical information in the medical information database 210. The input information includes, for example, the name, age, sex, address, occupation, chronic disease, and infection history of an owner. A screen 402 in FIG. 4B is an example of a screen displayed on the smartphone 250 to acquire such input information.

Before measurement using the medical measurement device 261 or 262, the application program 204 refers to the medical information database 210 to confirm whether the user of the smartphone 250 has a family. Similarly, the application program 204 confirms whether a plurality of measurement target persons may be measured using the same smartphone 250. If there are a plurality of measurement target persons in the family, the application program 204 displays a screen 403 shown in FIG. 4C on the display of the smartphone 250, and prompts the user to select a measurement target person.

Figure 4D:
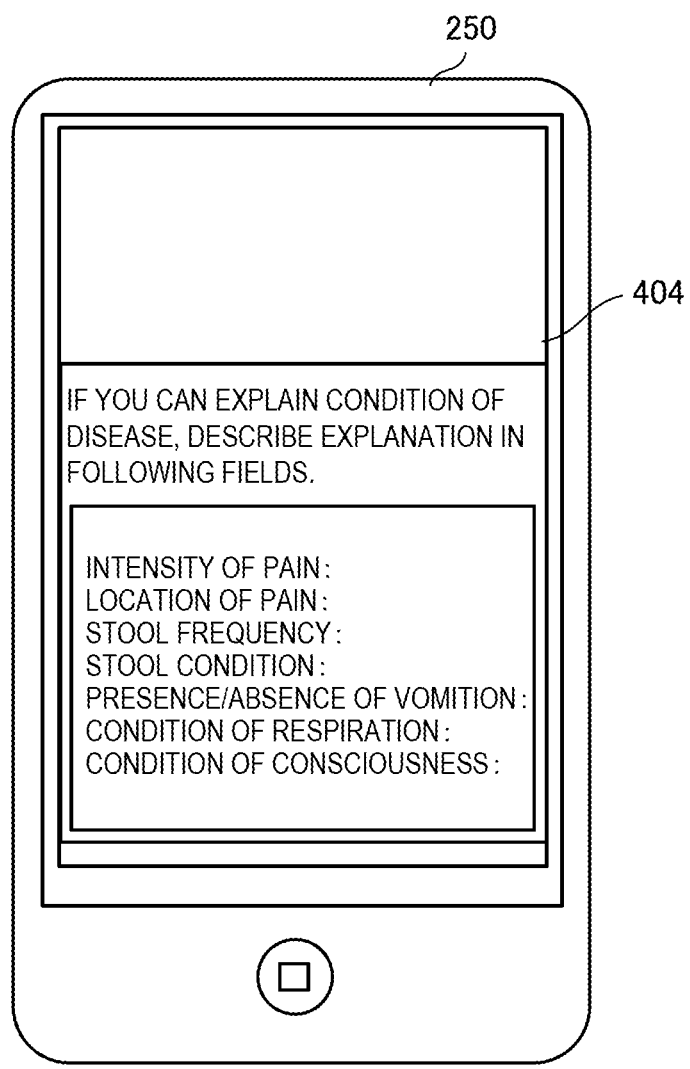
FIG. 4D is a view showing an example of a display screen displayed on the smartphone in the second embodiment of the present invention.
Figure 4F:
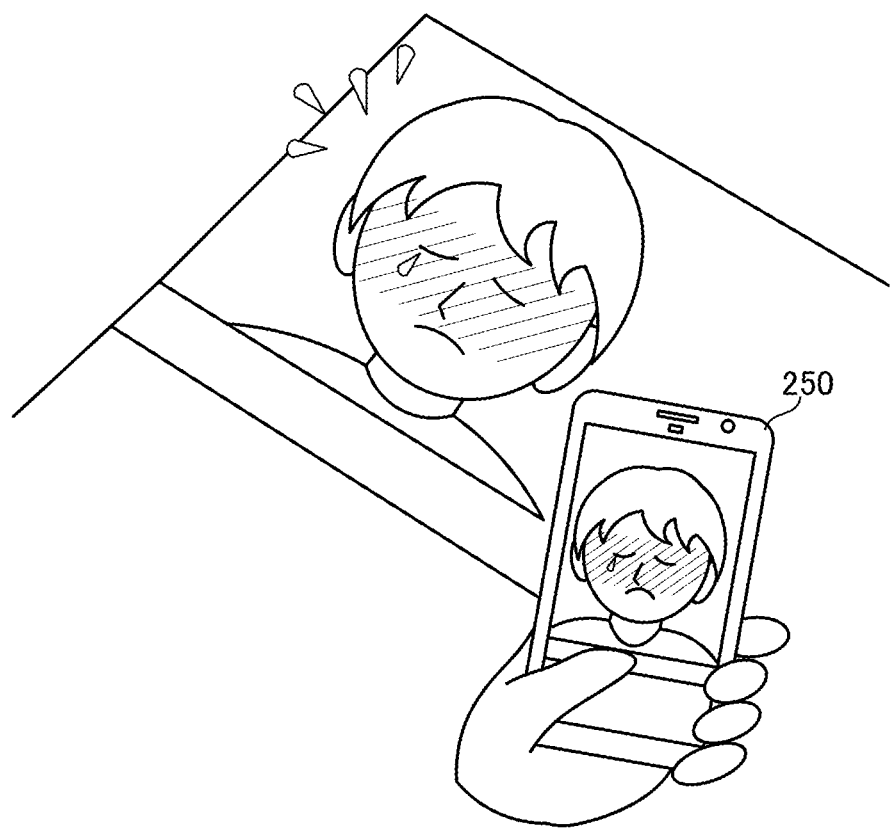
FIG. 4F is a view showing an example of a display screen displayed on the smartphone in the second embodiment of the present invention.

The application program 204 may display a screen 404 in FIG. 4D and allow the user of the smartphone 250 to input a free explanation, in order to acquire medical information unmeasurable by the medical measurement device 261 or 262. Examples of the input information are the location and intensity of a pain, the stool frequency and condition, the presence/absence of vomition, the way to see things, the condition of respiration, and consciousness/unconsciousness.

The application program 204 can also display a screen 405 shown in FIG. 4E after acquiring measurement information or after inputting input information. In this case, the application program 204 displays a message "To more accurately record the condition of a disease, you can photograph a measurement target person and transmit the image. Do you want to activate a camera application? Do you want to capture and register an image of the measurement target person?" If the user selects "YES", the application program 204 activates a camera application originally installed in the smartphone 250 and causes it to photograph the measurement target person (see FIG. 4F). The application program 204 links the photographed image or video with measurement result information (adds the same measurement ID), and transmits it to the cloud server 200.

Also, the application program 204 acquires environment information to be associated with the measurement result information from the smartphone 250. For example, the environment information includes a location (measurement location and behavior history) acquired using a GPS (Global Positioning System) function or the like mounted in the smartphone 250, the measurement time, and owner information of the smartphone 250.

Figure 4G:
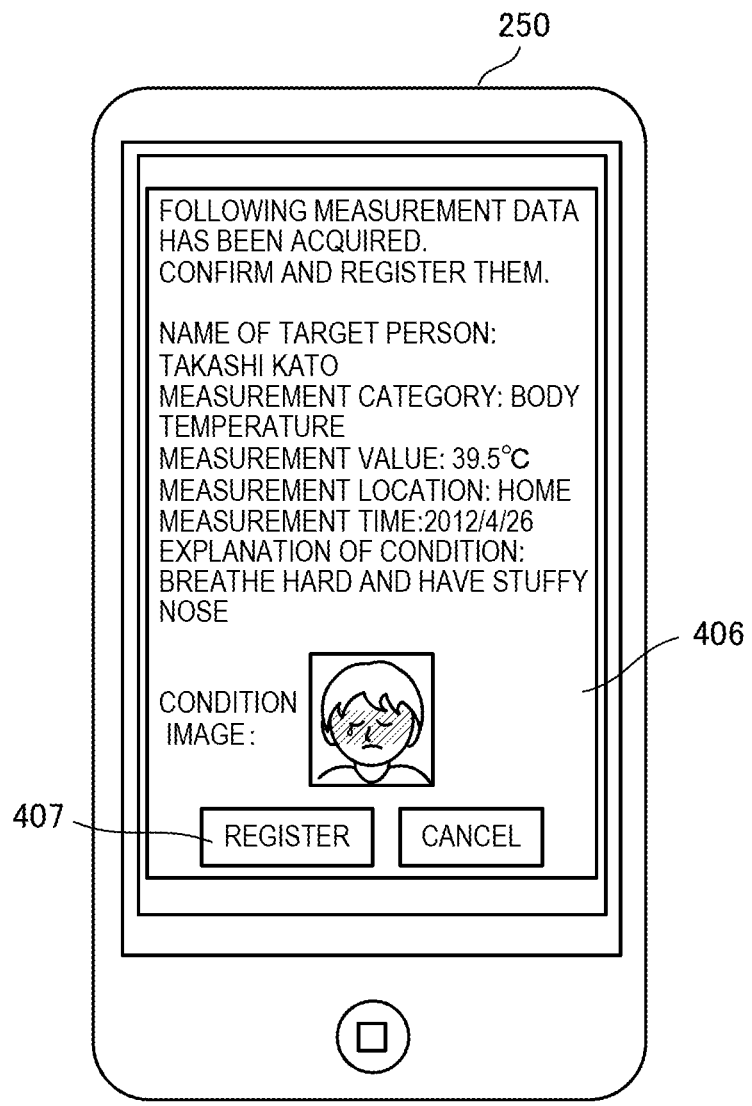
FIG. 4G is a view showing an example of a display screen displayed on the smartphone in the second embodiment of the present invention.
Figure 4H:
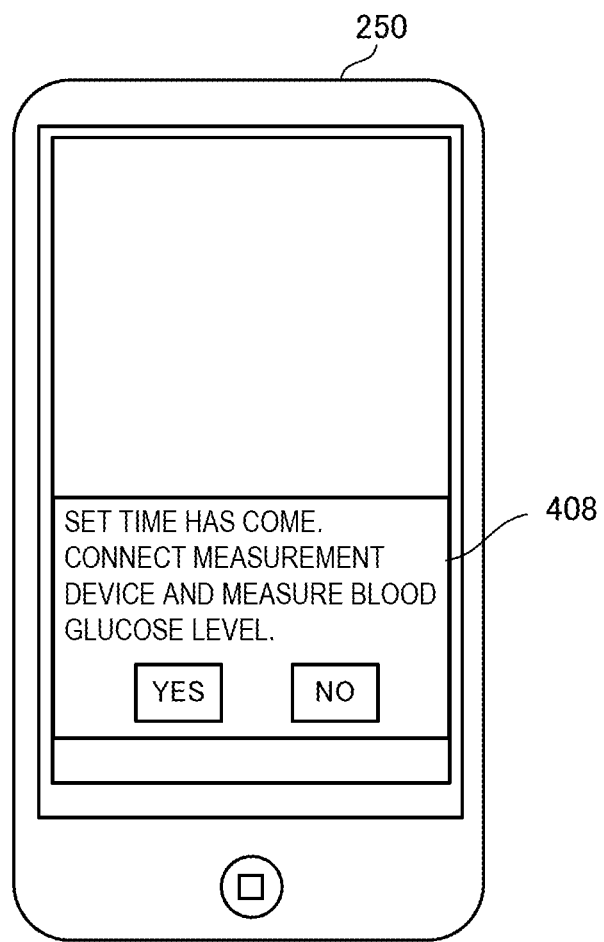
FIG. 4H is a view showing an example of a display screen displayed on the smartphone in the second embodiment of the present invention.

Upon completion of acquiring the measurement result information, the input information, and the environment information, the application program 204 generates a screen that compiles them, and sends it to the smartphone 250. For example, a confirmation screen 406 as in FIG. 4G is displayed on the display of the smartphone 250, and when the user presses a "register" button 407, is registered as medical information in the medical information database 210.

The application program 204 may have a timer function, and cause the smartphone 250 to display a screen that prompts the user to measure medical information in accordance with the lapse of a predetermined time. The user of the smartphone 250 can measure medical information by using the medical measurement device 261 or 262 without forgetting the measurement. For example, it is desirable to display a screen 408 shown in FIG. 4H in every predetermined time on the smartphone 250 of a user with diabetes.

Figure 4I:
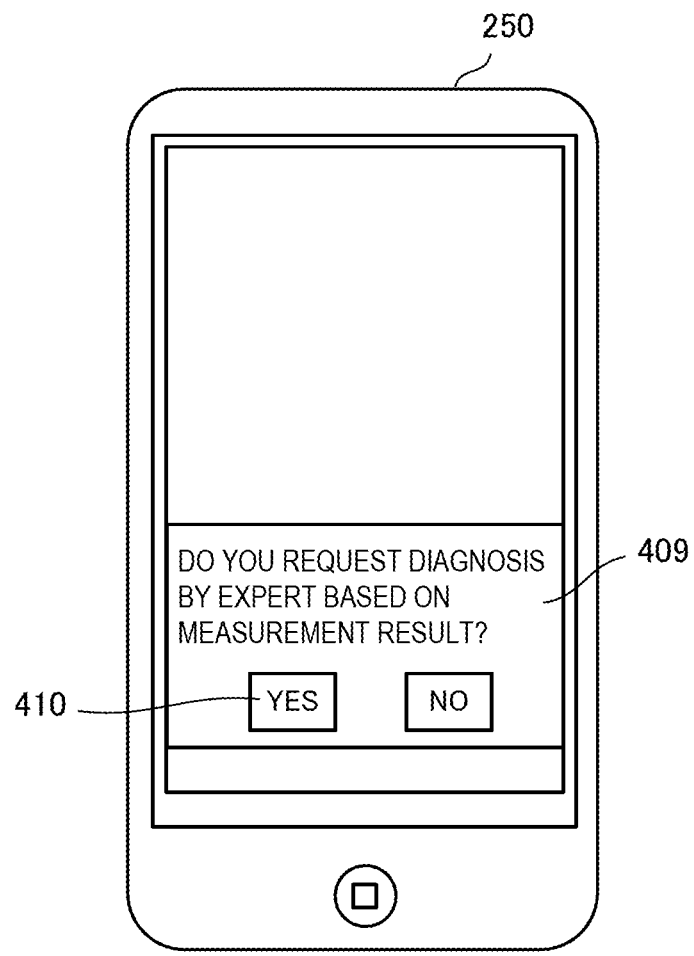
FIG. 4I is a view showing an example of a display screen displayed on the smartphone in the second embodiment of the present invention.
Figure 4J:
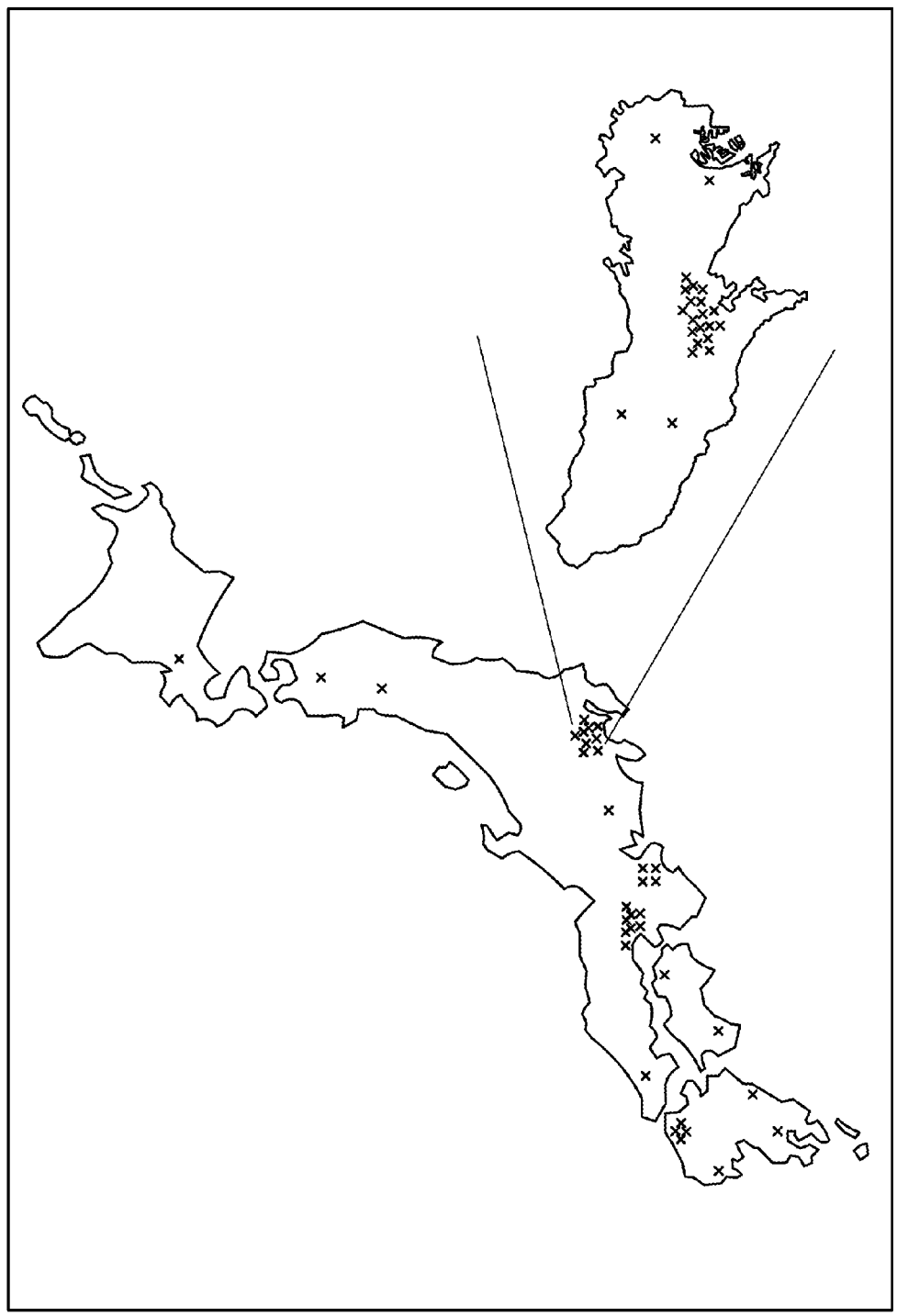
FIG. 4J is a view showing an example of a display screen displayed on a medical care worker communication terminal in the second embodiment of the present invention.

Further, the application program 204 displays a screen 409 as shown in FIG. 4I on the smartphone 250 to input whether to request a diagnosis after measurement. If the user of the smartphone 250 requests a diagnosis by pressing a "YES" button 410, the application program 204 transmits a diagnosis request to a medical care worker who has been registered in advance in the cloud server 200. At this time, an address in the medical information database 210 at which specifying information of a measurement target person or medical information of the measurement target person is stored is added to the diagnosis request. The diagnosis request may be transmitted to the medical care worker by using e-mail or by another method.

For example, when a URL dedicated to the measurement target person in the medical information database 210 is embedded in e-mail and transmitted to a medical care worker communication terminal 270, the medical care worker can access the URL to easily confirm the personal information, present condition, and medical history of the measurement target person. The medical care worker can access a global cloud server 295 by using the medical care worker communication terminal 270, and acquire global statistical medical information and the like. For example, the medical care worker can confirm the type of influenza and the location where it is prevalent. Alternatively, the medical care worker can access behavior history information of a user that has been registered in the cloud server 200, and search for the cause of the infection.

The medical care worker inputs a comment from the medical care worker communication terminal 270 to a comment input screen generated by the cloud server 200. A comment from the medical care worker such as "Stay in bed, and wait and see overnight.", "◯◯ is suspected of having otitis media. If he says he has a pain in the ear, bring him to an otolaryngologist quickly.", or "Go to an emergency hospital right now." is temporarily registered in the medical information database 210. The application program 204 generates e-mail in which this comment is embedded, and transmits it to the smartphone 250. Since the mail address of the medical care worker is hidden from the user, a trouble in which the user repetitively sends mail directly to the medical care worker can be avoided.

The cloud server 200 generates general medical information by deleting information capable of specifying an individual (part of the name and address) from personal medical information stored in the medical information database 210, and transmits the general medical information to the global cloud server 295. The global cloud server 295 generates statistical data by compiling pieces of general medical information collected from two or more local cloud networks 290. As the statistical data, for example, the location where influenza is prevalent can be obtained from the distribution of the measurement locations of body temperatures in a feverish condition, and can be displayed on the smartphone 250 and the medical care worker communication terminal 270 (see FIG. 4J). For example, the location of the cause of food poisoning can also be estimated by comparing the behavior histories of a plurality of measurement target persons suffering food poisoning (for example, abdominal pain, diarrhea, or fever).

Personal medical information accumulated in the cloud server 200 or general medical information collected and arranged in the global cloud server 295 is transmitted to and displayed on the smartphone 250 in response to a request from the smartphone 250.

When using the cloud server 200, the user of the smartphone 250 can set one of a plurality of service levels with different usage fees. The type of information acquirable by the smartphone 250 from the global cloud server 295 or the local cloud network 290 may be changed in accordance with the service level.

(Processing Sequence of Overall System)

Figure 5:
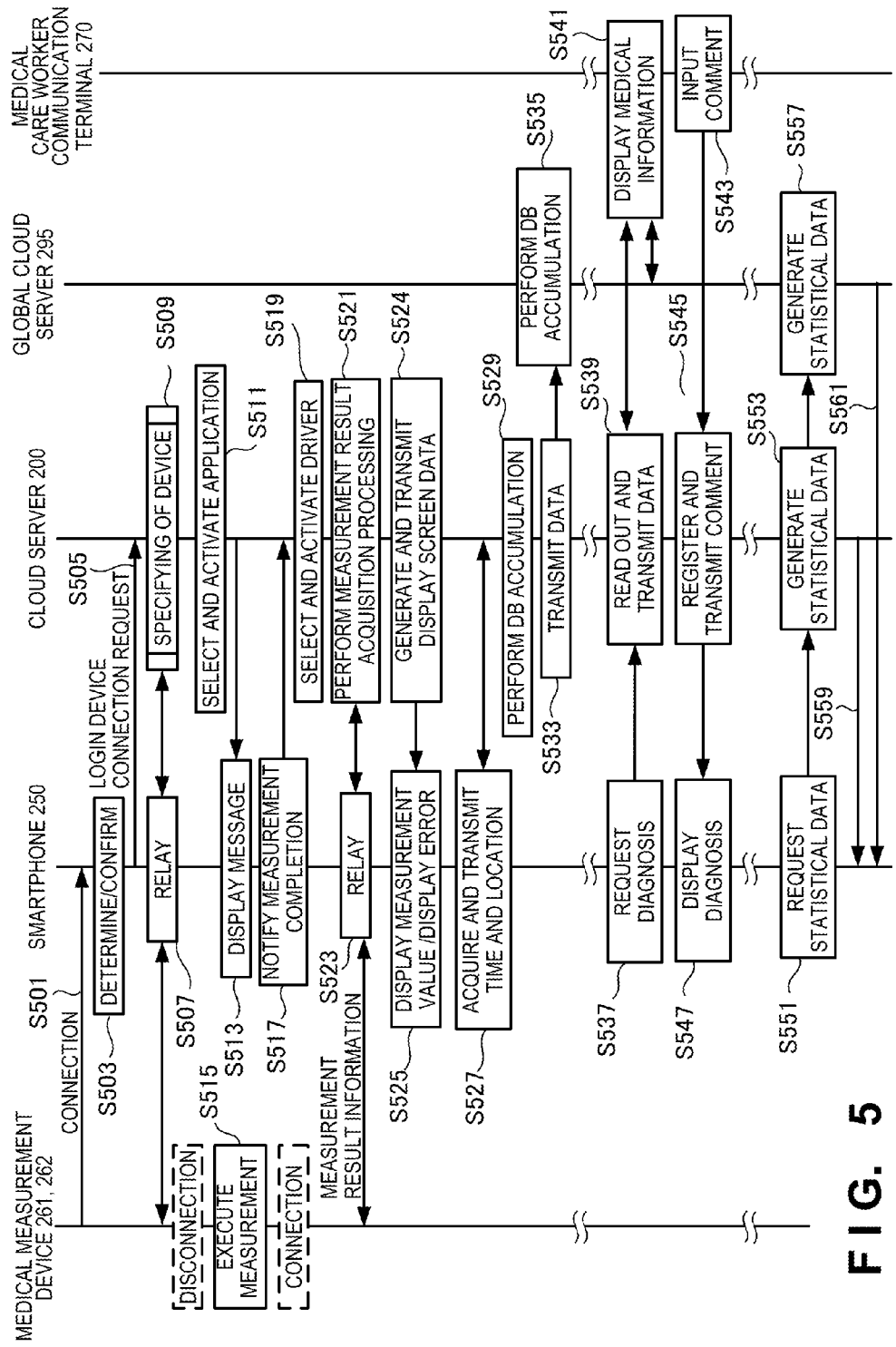
FIG. 5 is a sequence chart showing the processing sequence of the overall information processing system according to the second embodiment of the present invention.

The processing sequence of the overall system will be summarized next with reference to a sequence chart shown in FIG. 5. First, a medical measurement device (for example, the blood pressure/pulse measurement device 261 or the body temperature measurement device 262) is connected to the smartphone 250 (S501). In response to the connection as a trigger, the smartphone 250 determines whether the local terminal includes a driver program and application program for acquiring measurement information from the medical measurement device 261 or 262.

The capacity of the smartphone 250 does not suffice for downloading and installing the driver programs and application programs of various kinds of medical measurement devices 261 and 262. For this reason, after confirmation by a user, as shown in FIG. 4A, the user logs in to the cloud server 200 from the smartphone 250, and requests to acquire measurement result information from the medical measurement device 261 or 262 under the initiative of the cloud server 200 (S505). However, the user of the smartphone 250 needs to be a member of a cloud provider who runs the cloud server 200.

The cloud server 200 specifies the medical measurement device 261 or 262 through exchange with the medical measurement devices 261 and 262 via the smartphone 250 (S509). Then, the cloud server 200 selects and activates an application program 204 corresponding to the medical measurement device 261 or 262 (S511). This application displays a message on the display of the smartphone 250 (S513). A conceivable example of the message at this time is "The server is ready. Operate a sphygmomanometer normally to measure a blood pressure and pulse, and after the measurement, click the measurement completion button below." A message "The server is ready. Remove a USB cable from a clinical thermometer, measure a body temperature, then connect the USB cable, and click the measurement completion button below." may also be displayed. In any case, a message desirably copes with the device specified in step S509.

The measurement target person or the owner of the smartphone 250 executes measurement (S515), and after confirming the completion of measurement, operates the smartphone 250 to transmit a measurement completion notification to the cloud server 200 (S517). In the above-described case, when the user clicks the "measurement completion" button displayed on the screen of the smartphone 250, the measurement completion notification is sent from the smartphone 250 to the cloud server 200.

The cloud server 200 selects a driver corresponding to the device specified in step S509 from a driver program database (S519). The cloud server 200 activates the driver to access the medical measurement device 261 or 262 via the smartphone 250 and acquire measurement result information (S521). At this time, IP (Internet Protocol) is used between the smartphone 250 and the cloud server 200, and the USB protocol is used between the smartphone 250 and the medical measurement device 261 or 262. The smartphone 250 performs encapsulation and decapsulation of these protocols as relay processing (S523).

In step S525, the cloud server 200 generates display screen data and transmits it to the smartphone 250. More specifically, when a measurement result can be acquired normally, the cloud server 200 performs display processing of the measurement result. If an error occurs in acquiring a measurement result or if it is determined that the measurement result is less reliable, the cloud server 200 displays an error.

Then, the cloud server 200 acquires information about the time and location from the smartphone 250 (S527). These pieces of information are transmitted together with the same ID as that of the measurement result, and accumulated in the database in association with the measurement result, the time, the location, and the like in step S529 (S531).

In every predetermined period or after a predetermined amount of data is accumulated, the cloud server 200 transmits, to the global cloud server 295, data from which personal information has been deleted (S533). The global cloud server 295 accumulates the data received from the cloud server 200 in the database (S535).

By the above-described series of processes, the cloud server 200 and the global cloud server 295 can accumulate the measurement result regarding medical care as knowledge. Although not shown here, the measurement target person information (for example, name and address) and attending doctor information (for example, name, division, and address) can be transmitted to the cloud server 200 in response to a free access from the smartphone 250. The cloud server 200 stores these pieces of information in the medical information database 210 in association with each other.

If a diagnosis request is transmitted from the smartphone 250 (S537), the cloud server 200 reads out the measurement result information accumulated in the database, and transmits it to the medical care worker communication terminal 270 associated with the measurement target person. Upon receiving the measurement result information, the medical care worker communication terminal 270 accepts a comment input from a medical care worker (S543), and transmits the accepted comment to the cloud server 200. Upon accepting registration of the comment from the medical care worker, the cloud server 200 transmits the comment to the smartphone 250 (S545). The smartphone 250 displays the comment as a diagnosis by the medical care worker (S547).

In this manner, when exchanging information between the smartphone 250 and the medical care worker communication terminal 270, the cloud server 200 acquires location information of the smartphone 250 and location information of the medical care worker communication terminal 270, and corrects the time in consideration of the time difference. That is, when transmitting information to the medical care worker communication terminal 270, the time included in measurement result information is converted into a local time complying with the location of the medical care worker communication terminal 270. Also, when transmitting a comment to the smartphone 250, a local time complying with the location of the smartphone 250 is used as the time when the comment was input. Accordingly, medical cooperation can be easily performed between regions having a time difference. The cloud server 200 may propose, from a medical care worker database (not shown) to the user of the smartphone 250, a medical care worker frequently selected in the same hospital or the same area based on the address of a measurement target person, a hospital to which the measurement target person is admitted or goes, the name of a health organization, or the like. Further, the evaluation of the medical care worker by the user of the smartphone 250 may be accumulated as knowledge.

The smartphone 250 can request statistical data (S551). In response to this request, the cloud server 200 or the global cloud server 295 generates statistical data (S553 or S557), and transmits it to the smartphone 250 (S559 or S561).

By the above-described processing, the user of the smartphone 250 signs on to and signs up to a cloud service, and then can receive a comment from a medical care worker and acquire statistical medical information and information such as a comparison between his symptom and the condition of others.

<<Functional Arrangement of Cloud Server>>

FIG. 6 is a block diagram showing the functional arrangement of the cloud server 200 according to this embodiment. The cloud server 200 includes a communication controller 601 that communicates with the smartphone 250 via a network. A descriptor receiver 602 receives, from a message received from the smartphone 250 by the communication controller 601, a descriptor acquired from the medical measurement device 261 or 262 connected to the smartphone 250. A device determinator 603 specifies the medical measurement device 261 or 262 connected to the smartphone 250 by referring to a device database 623 (see FIG. 7E) from the device descriptor received from the smartphone 250.

Based on device information from the device determinator 603, a program selector 606 selects a device driver program and an application program by referring to a driver program database 624 and an application program database 625.

An application executor 607 executes the application selected by the program selector 606. The application executor 607 generates an operation screen to be transmitted to the smartphone 250, and transfers it to an operation screen transmitter 608. The operation screen transmitter 608 transmits the operation screen to the smartphone 250. An operation instruction receiver 609 receives an operation instruction transmitted from the smartphone 250. The operation instruction receiver 609 transfers the received operation instruction to the application executor 607. The application executor 607 outputs a device driving instruction to a USB device driver executor 610 so as to perform the operation of the medical measurement device 261 or 262 according to the operation instruction.

The USB device driver executor 610 executes the device driver selected by the program selector 606. The USB device driver executor 610 generates a USB packet to be transmitted to the medical measurement device connected via the smartphone 250, and transfers it to a USB packet encapsulator 611. The USB packet encapsulator 611 performs IP encapsulation of the USB packet and transmits the USB packet to the smartphone 250. A USB packet decapsulator 612 receives a message transmitted from the smartphone 250 upon IP encapsulation, and decapsulates the message. The USB device driver executor 610 analyzes the received USB packet, generates a new USB packet, responds to the medical measurement device, and reports the device status to the application executor 607.

When the received USB packet is measurement result information by the medical measurement device 261 or 262, the USB device driver executor 610 transfers the measurement result information to a measurement result information receiver 613. The measurement result information receiver 613 transfers the measurement result information to a medical information generator 615.

The cloud server 200 also includes an input information receiver 614 and an environment information receiver 616. The input information receiver 614 and the environment information receiver 616 receive input information and environment information from the smartphone 250, respectively, and transfer them to the medical information generator 615. The medical information generator 615 generates medical information by compiling the received measurement result information, input information, and environment information, and registers the medical information in the medical information database 210.

The medical information generator 615 may be part of the application executor 607. In this case, the application program 204 is executed to acquire measurement result information, input information, and environment information, generate medical information, and accumulate the medical information in the medical information database 210.

(Processing Sequence in Cloud Server 200)

Figure 7A:
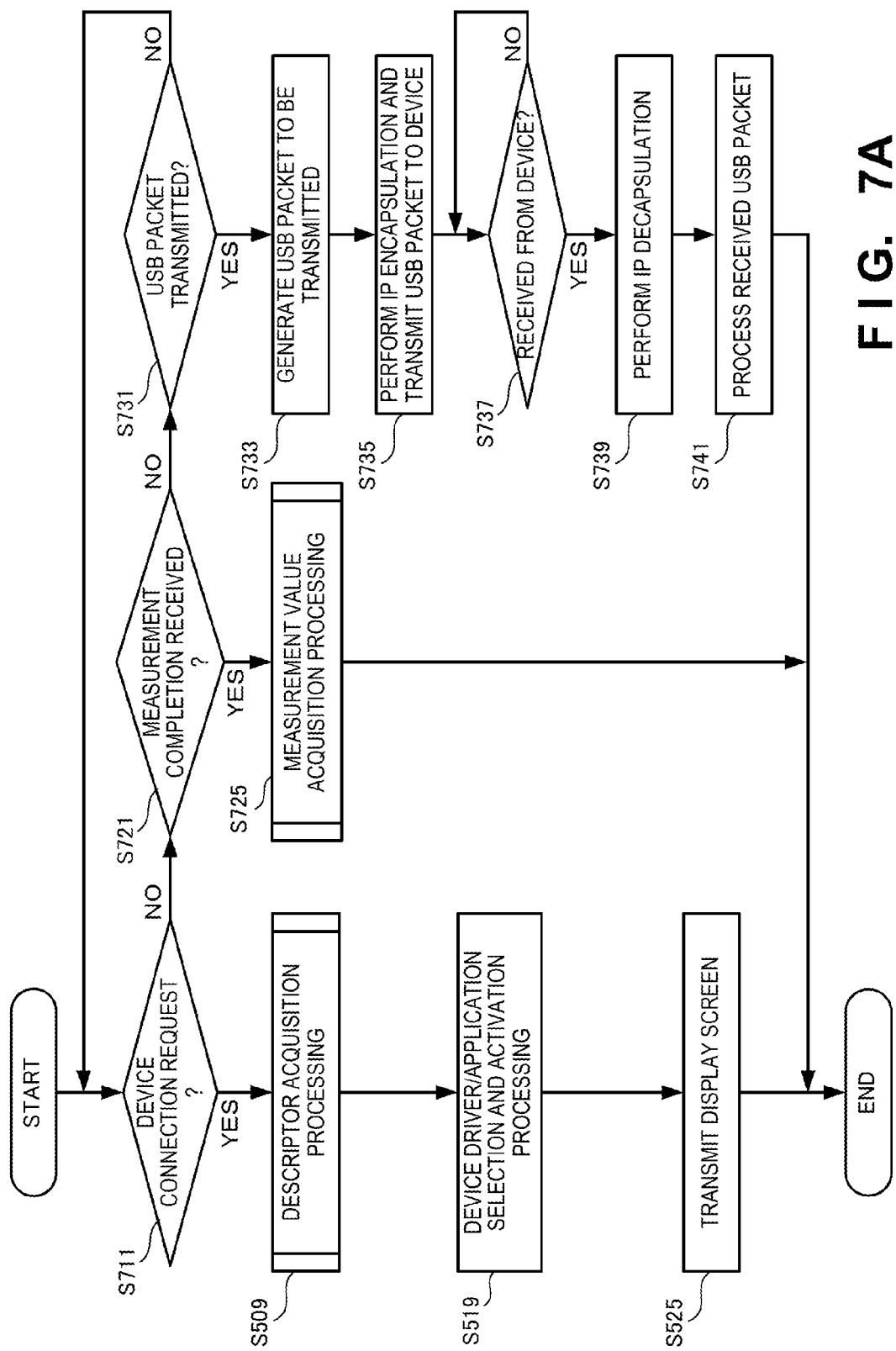
FIG. 7A is a flowchart showing a processing sequence in the cloud server in the second embodiment of the present invention.

A more detailed processing sequence in the cloud server 200 will be explained with reference to FIG. 7A. If the cloud server 200 determines in step S711 that it has received a device connection request from the smartphone 250, it advances to step S509 to perform descriptor acquisition processing. The cloud server 200 selects a device driver and an application program based on an acquired descriptor, and activates them (S519). Further, the cloud server 200 transmits a predetermined display screen to the smartphone 250 along with execution of the application program 204.

If the cloud server 200 determines in step S721 that it has received a measurement completion notification, it performs measurement result acquisition processing in step S725.

If the cloud server 200 determines in step S731 to transmit a USB packet, it advances to step S733 to generate a USB packet to be transmitted, and to step S735 to perform IP encapsulation and transmit the USB packet. After that, the cloud server 200 waits for reception of a USB packet from the device (S737), and if it receives a USB packet, performs IP decapsulation (S739) and processes the received USB packet (S741).

<Descriptor Acquisition Method>

Figure 7C:
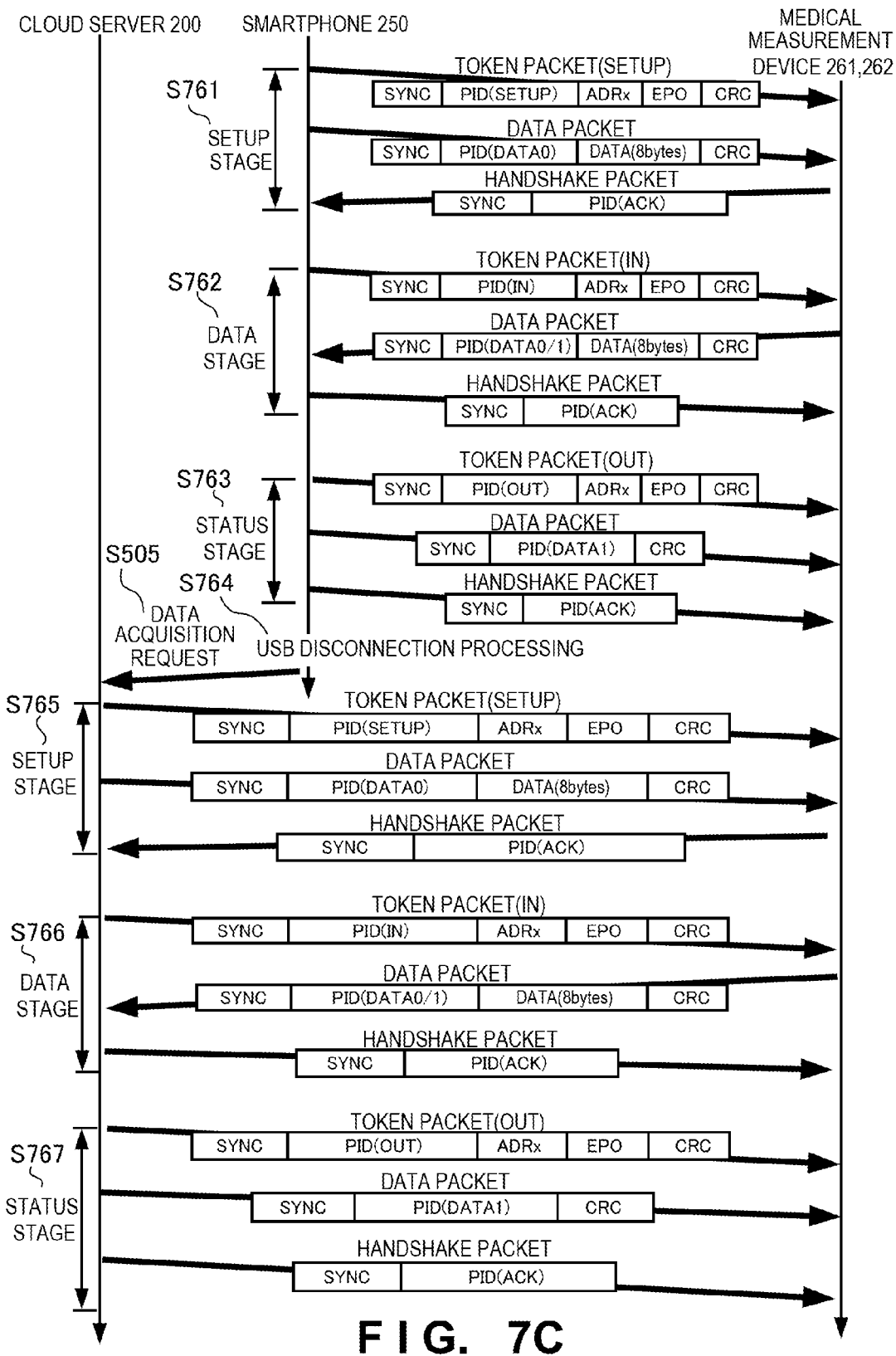
FIG. 7C is a chart showing another example of packet transmission/reception processing in the information processing system according to the second embodiment of the present invention.
Figure 7D:
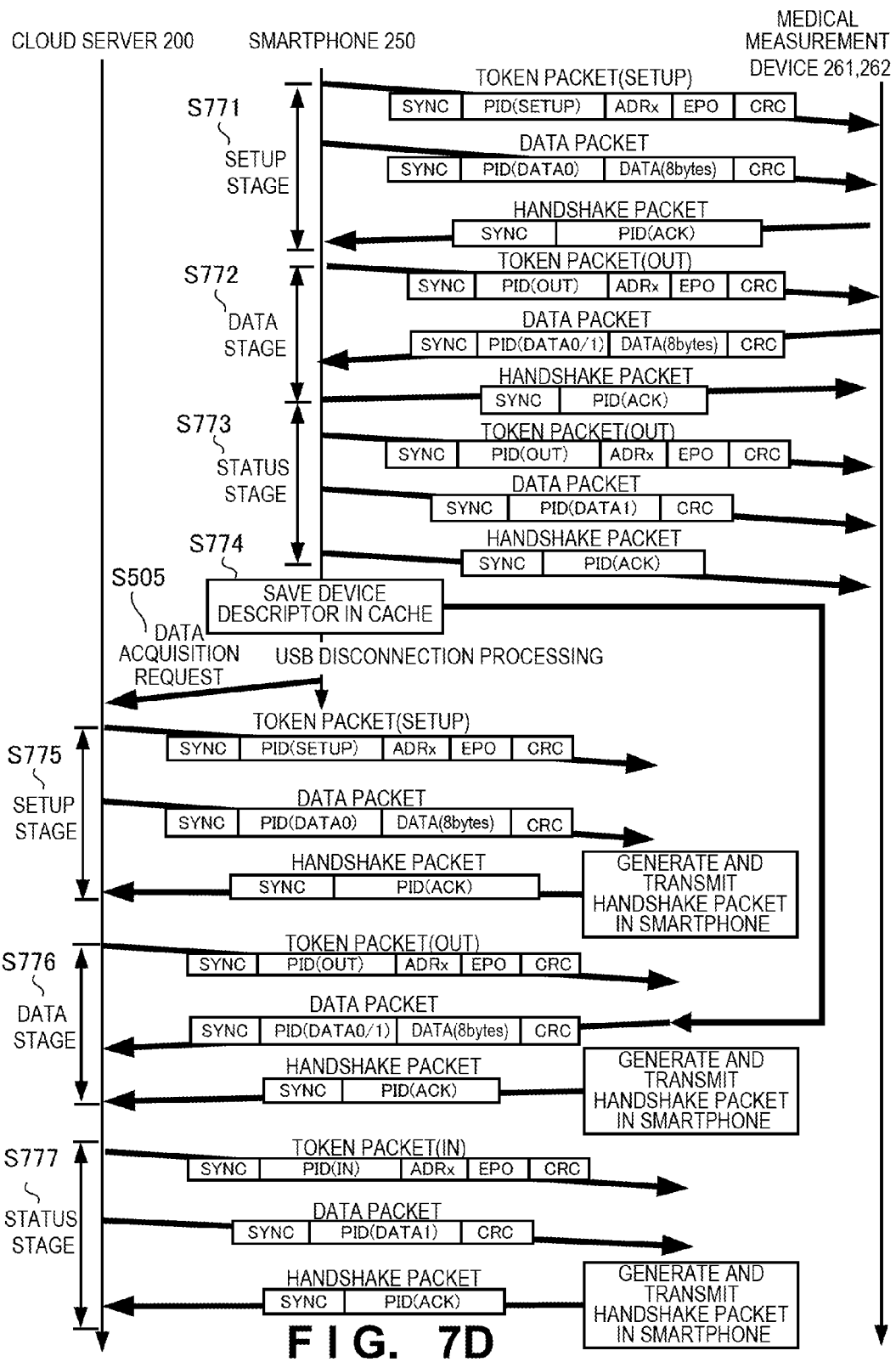
FIG. 7D is a chart showing still another example of packet transmission/reception processing in the information processing system according to the second embodiment of the present invention.

FIGS. 7B, 7C, and 7D are charts for explaining in more detail exchange of the descriptor explained in step S509. These drawings show packet data exchanged between the cloud server 200, the smartphone 250, and the medical measurement device 261 or 262.

In FIG. 7B, when the medical measurement device 261 or 262 is connected to the smartphone 250, a token packet and a data packet are transmitted from the smartphone 250 to the medical measurement device 261 or 262 in setup stage S751. In response to this, the medical measurement device 261 or 262 transmits a handshake packet to the smartphone 250. Whether the local terminal can control the medical measurement device 261 or 262 is determined based on whether a proper handshake packet is returned.

For example, if a device assumes in advance a connection to the smartphone 250, a proper handshake packet is returned, and a data stage and a status stage continue. The medical measurement device can be controlled by driving a device driver prepared in the smartphone 250 in correspondence with the acquired device descriptor. However, very few medical measurement devices assume a connection to the smartphone 250. If no handshake packet is returned in setup stage S701, USB disconnection processing is performed (S752), and the smartphone 250 transmits a data acquisition request to the cloud server 200 (S505).

Then, the cloud server 200 performs again setup stage S703 with the medical measurement device 261 or 262 via the smartphone 250, and advances to data stage S704 to acquire device information such as a device descriptor. The cloud server 200 is equipped in advance with many drivers and data conversion modules so that it can be connected to various medical measurement devices 261 and 262 present in the world. Thus, setup stage S753, data stage S754, and status stage S755 smoothly proceed between the cloud server 200 and the medical measurement device 261 or 262, and a connection with the medical measurement device 261 or 262 is established appropriately.

FIG. 7C shows a sequence in a case in which the medical measurement device 261 or 262 sends back a handshake packet, but the smartphone 250 does not have a driver corresponding to a device descriptor acquired from the medical measurement device 261 or 262. In this case, setup stage S761, data stage S762, and status stage S763 are performed between the smartphone 250 and the medical measurement device 261 or 262. If it is determined that the smartphone 250 does not have a device driver corresponding to a device descriptor acquired through these three stages, USB disconnection processing S764 is performed. Then, the smartphone 250 transmits a data acquisition request to the cloud server 200 (S505).

The smartphone 250 requests, of the cloud server 200, a connection to the medical measurement device 261 or 262. After the USB connection between the smartphone 250 and the medical measurement device 261 or 262 is disconnected, the cloud server 200 performs again setup stage S765, data stage S766, and status stage S767. As a result, the cloud server 200 can directly acquire a device descriptor from the medical measurement device 261 or 262, and drive a driver corresponding to the device.

FIG. 7D shows processing when a device descriptor acquired in setup stage S771 and data stage S772 between the smartphone 250 and the medical measurement device 261 or 262 is cached in the smartphone 250. Before performing USB disconnection processing, the acquired device descriptor is cached in the smartphone 250 (S774). The smartphone 250 transmits a data acquisition request to the cloud server 200 (S505).

After the connection between the smartphone 250 and the medical measurement device 261 or 262 is temporarily disconnected, connection establishment processing with the medical measurement device 261 or 262 starts under the initiative of the cloud server 200 (S775 to S777). In this case, in setup stage S775, the smartphone 250 generates a handshake packet and transmits it to the cloud server 200 without transmitting a setup token packet and a data packet to the medical measurement device 261 or 262. In data stage S776, the smartphone 250 receives a token packet and a data packet from the cloud server 200. The smartphone 250 reads out the device descriptor from the cache and transmits it to the cloud server 200 without transmitting these packets to the medical measurement device 261 or 262. Since processing of acquiring a device descriptor from the medical measurement device 261 or 262 can be omitted, the process can efficiently restart after communication disconnection from the medical measurement device 261 or 262.

(Medical Measurement Device Specifying Table)

As shown in FIG. 7E, the device database 623 stores the correspondence between a device descriptor, an interface descriptor, a vendor ID, and a product ID.

When a medical measurement device is connected, the cloud server 200 searches the device database 623 for a device descriptor acquired from the medical measurement device via the smartphone 250, and specifies a corresponding vendor ID and product ID. The cloud server 200 selects a device driver corresponding to the vendor ID and product ID from the driver program database 624, and executes it.

Note that the device database 623 stores the correspondence between a device descriptor, an interface descriptor, a vendor ID, and a product ID, but the present invention is not limited to this. For example, the device database 623 may further store the correspondence between a device descriptor and a trade name. In this case, the trade name of a medical measurement device may be specified from a device descriptor by using the device database 623, and displayed on the screen of the smartphone 250. The user of the smartphone 250 can confirm that the cloud server 200 has recognized the medical measurement device connected by him, and can feel greatly assured.

(USB Connection Processing)

Signals to be exchanged between the cloud server 200, the smartphone 250, and the medical measurement device 261 or 262 until USB communication is established will be explained in more detail with reference to FIGS. 8A to 8D. Particularly, an example in which a device descriptor is saved in the cache, as described with reference to FIG. 7D, will be explained.

In step S801, the medical measurement device 261 or 262 is connected to the smartphone 250 and turned on. In step S802, the smartphone 250 starts USB connection processing to the medical measurement device 261 or 262, and transmits a reset signal. In step S803, the smartphone 250 designates an address to the medical measurement device 261 or 262. This address is added to packets to be subsequently exchanged between the smartphone 250 and the medical measurement device 261 or 262.

In step S804, the smartphone 250 performs "GET DESCRIPTOR" processing to acquire a descriptor from the medical measurement device 261 or 262. The "GET DESCRIPTOR" processing is the same as that in steps S721 to S723 described with reference to FIG. 7D, and thus is not explained in detail. After the smartphone 250 transmits a descriptor request to the medical measurement device 261 or 262 (S805), the medical measurement device 261 or 262 transmits, to the smartphone 250, a device descriptor stored in an end point 0 area (S806 and S807). In status stage S723, the smartphone 250 transmits an acknowledge signal (ACK) to the medical measurement device 261 or 262.

Upon acquiring the device descriptor, the smartphone 250 saves it in the cache (S724). By using the device descriptor, the smartphone 250 determines whether it can control the device (S505). If the smartphone 250 determines that it cannot control the device, it advances to step S811 to perform USB disconnection processing. At the same time, the smartphone 250 requests the cloud server 200 to control the medical measurement device 261 or 262 (S812).

In step S813, the cloud server 200 starts processing to control the medical measurement device 261 or 262, and transmits a reset signal to the medical measurement device 261 or 262 via the smartphone 250. In step S815, the cloud server 200 performs SET ADDRESS and designates an address to the medical measurement device 261 or 262.

Further, the cloud server 200 performs GET DESCRIPTOR (S816) and GET CONFIGURATION (S824) to the medical measurement device 261 or 262 via the smartphone 250 (S823). More specifically, in step S817, the cloud server 200 sends a get descriptor to the smartphone 250. In step S819, the smartphone 250 reads out the device descriptor saved in the cache, and transmits it to the cloud server 200.

In step S825, the medical measurement device 261 or 262 transmits a configuration descriptor stored in the end point 0 area. Then, the cloud server 200 performs BULK TRANSFER to the medical measurement device 261 or 262 via the smartphone 250 (S826). Then, the medical measurement device 261 or 262 reads out measurement result information (S827), and transmits it to the cloud server 200 via the smartphone 250. If the smartphone 250 determines in step S503 based on the device descriptor of the medical measurement device 261 or 262 that the medical measurement device 261 or 262 is not a controllable device, it advances to step S828 of FIG. 8B. In steps S828 and S829, configuration descriptor acquisition processing is performed. In response to this, the medical measurement device 261 or 262 transmits the configuration descriptor to the smartphone 250. In step S832, the smartphone 250 saves the acquired configuration descriptor in the cache. In step S503, the smartphone 250 determines based on the configuration descriptor whether the medical measurement device 261 or 262 is a device controllable by the smartphone 250. If the smartphone 250 determines that the medical measurement device 261 or 262 is not controllable, it advances to step S833 to disconnect the USB connection between the smartphone 250 and the medical measurement device 261 or 262.

After the USB connection is disconnected, the smartphone 250 requests the cloud server 200 to control the medical measurement device 261 or 262. In response to this control request, the cloud server 200 starts USB control, and transmits a reset signal to the medical measurement device 261 or 262 via the smartphone 250 (S835). Subsequently, the cloud server 200 performs SET ADDRESS (S836), and designates an address to the medical measurement device 261 or 262. Further, the cloud server 200 requests a descriptor of the smartphone 250 by GET DESCRIPTOR (S837). The smartphone 250 reads out the device descriptor from the cache (S839), and sends it back to the cloud server 200 (S840), instead of relaying the request to the medical measurement device 261 or 262.

Further, the cloud server 200 executes GET CONFIGURATION to the medical measurement device 261 or 262 via the smartphone 250 (S841). The smartphone 250 reads out the configuration descriptor stored in the cache, and transmits it to the cloud server 200 (S843), instead of transmitting the command to the medical measurement device 261 or 262. Then, the cloud server 200 performs BULK TRANSFER to the medical measurement device 261 or 262 via the smartphone 250 (S844). The medical measurement device 261 or 262 reads out measurement result information (S845), and transmits it to the cloud server 200 via the smartphone 250.

Figure 8C:
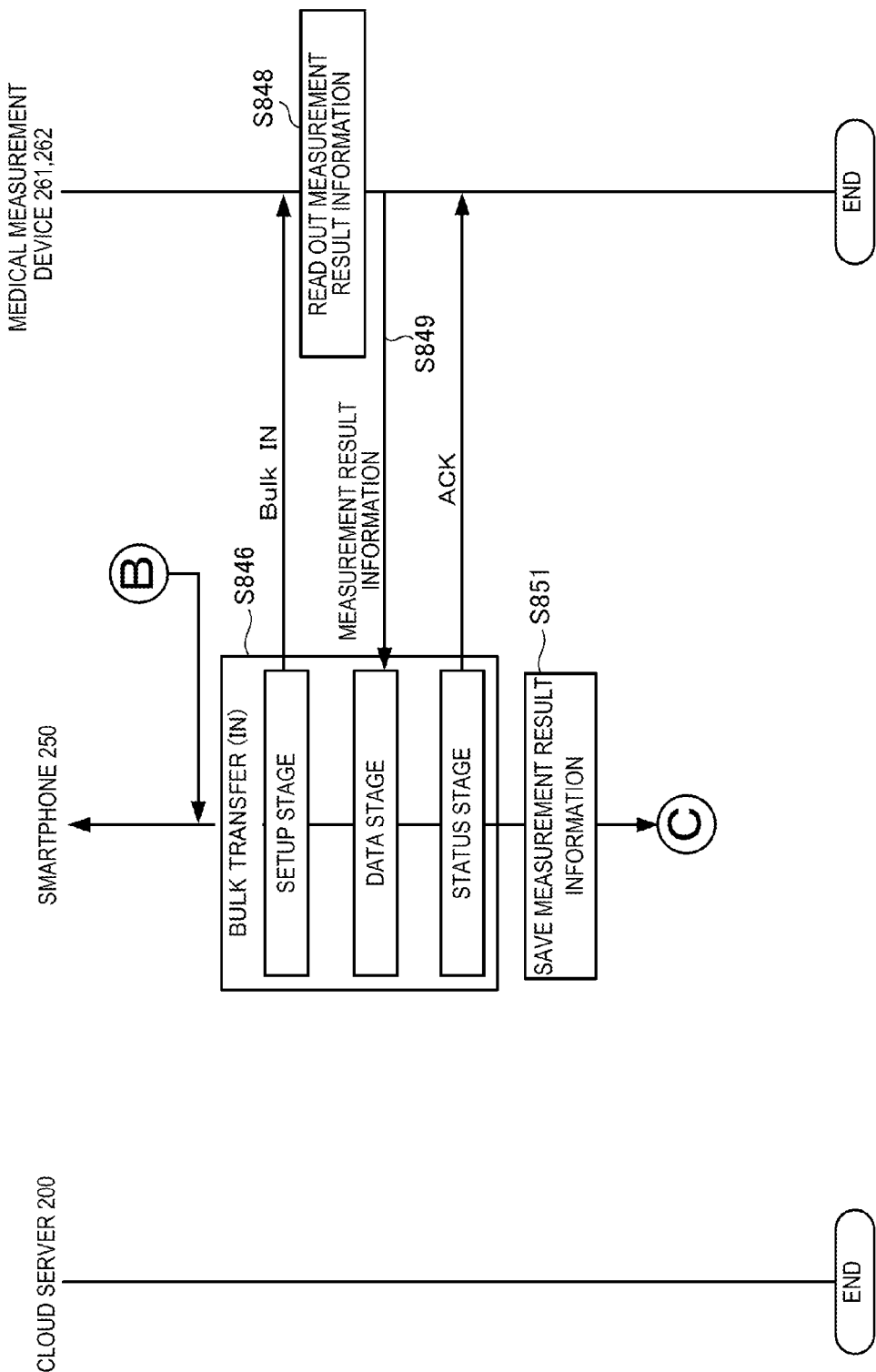
FIG. 8C is a chart showing the example of communication establishment processing between the server and the device in the information processing system according to the second embodiment of the present invention.

If the smartphone 250 determines in step S505 based on the configuration descriptor that the medical measurement device 261 or 262 is a controllable device (B), it advances to BULK TRANSFER in step S846 of FIG. 8C. Even in BULK TRANSFER, the setup stage, the data stage, and the status stage are performed to read out measurement result information from the medical measurement device 261 or 262 and transmit it to the smartphone 250 (S849).

Upon receiving the readout measurement result information, the smartphone 250 saves it in the cache (S851), and determines whether there is an application capable of performing display processing on the measurement result information (S852).

If the smartphone 250 determines that the measurement result information is processable, it advances to step S853 to continue the processing without accessing the cloud server 200. In this case, the smartphone 250 can directly reproduce the measurement result information of the medical measurement device 261 or 262.

Figure 8D:
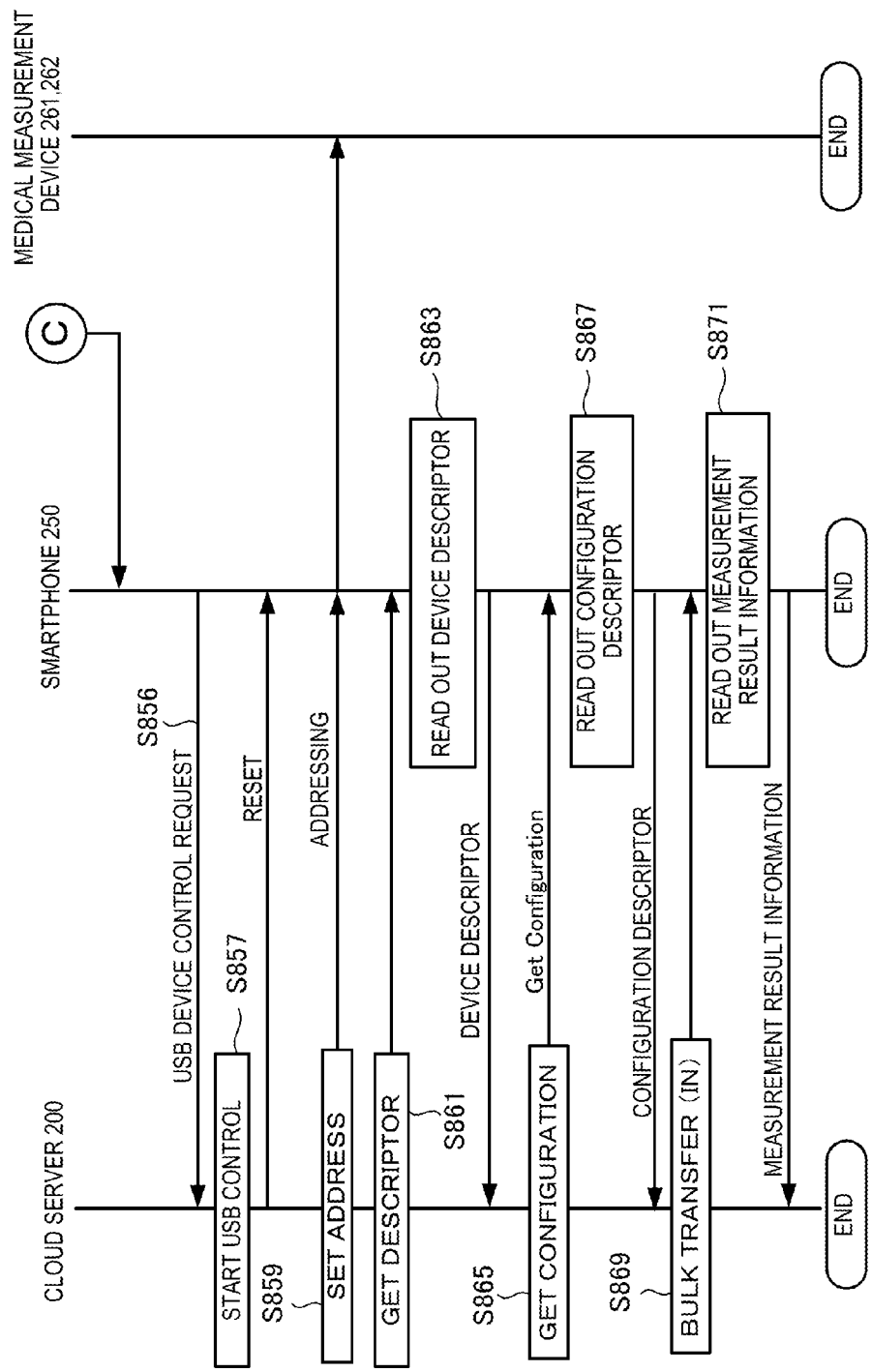
FIG. 8D is a chart showing the example of communication establishment processing between the server and the device in the information processing system according to the second embodiment of the present invention.

If the smartphone 250 does not have an application capable of processing the measurement result information of the medical measurement device 261 or 262, it advances to step S854 to perform disconnection processing of the USB connection, and further advances to step S856 of FIG. 8D.

In step S856 of FIG. 8D, the smartphone 250 requests USB device control of the cloud server 200. The smartphone 250 requests the cloud server 200 to control the medical measurement device 261 or 262. The cloud server 200 starts USB control in response to this control request, and transmits a reset signal to the medical measurement device 261 or 262 via the smartphone 250 (S857). Then, the cloud server 200 performs SET ADDRESS (S859), and designates an address to the medical measurement device 261 or 262. The cloud server 200 requests a descriptor of the smartphone 250 by GET DESCRIPTOR (S861). The smartphone 250 reads out the device descriptor from the cache (S863), and sends it back to the cloud server 200, instead of relaying the request to the medical measurement device 261 or 262.

Further, the cloud server 200 executes GET CONFIGURATION to the medical measurement device 261 or 262 via the smartphone 250 (S865). The smartphone 250 reads out the configuration descriptor saved in the cache, and transmits it to the cloud server 200 via the smartphone 250 (S867), instead of relaying the command.

The cloud server 200 performs BULK TRANSFER to the medical measurement device 261 or 262 via the smartphone 250 (S869). The smartphone 250 reads out the measurement result information saved in the cache (S871), and transmits it to the cloud server 200.

According to the above-described sequence, communication between the cloud server 200 and the medical measurement device 261 or 262 can be efficiently performed by appropriately using the cache of the smartphone 250.

(Measurement Result Acquisition Processing)

Figure 9:
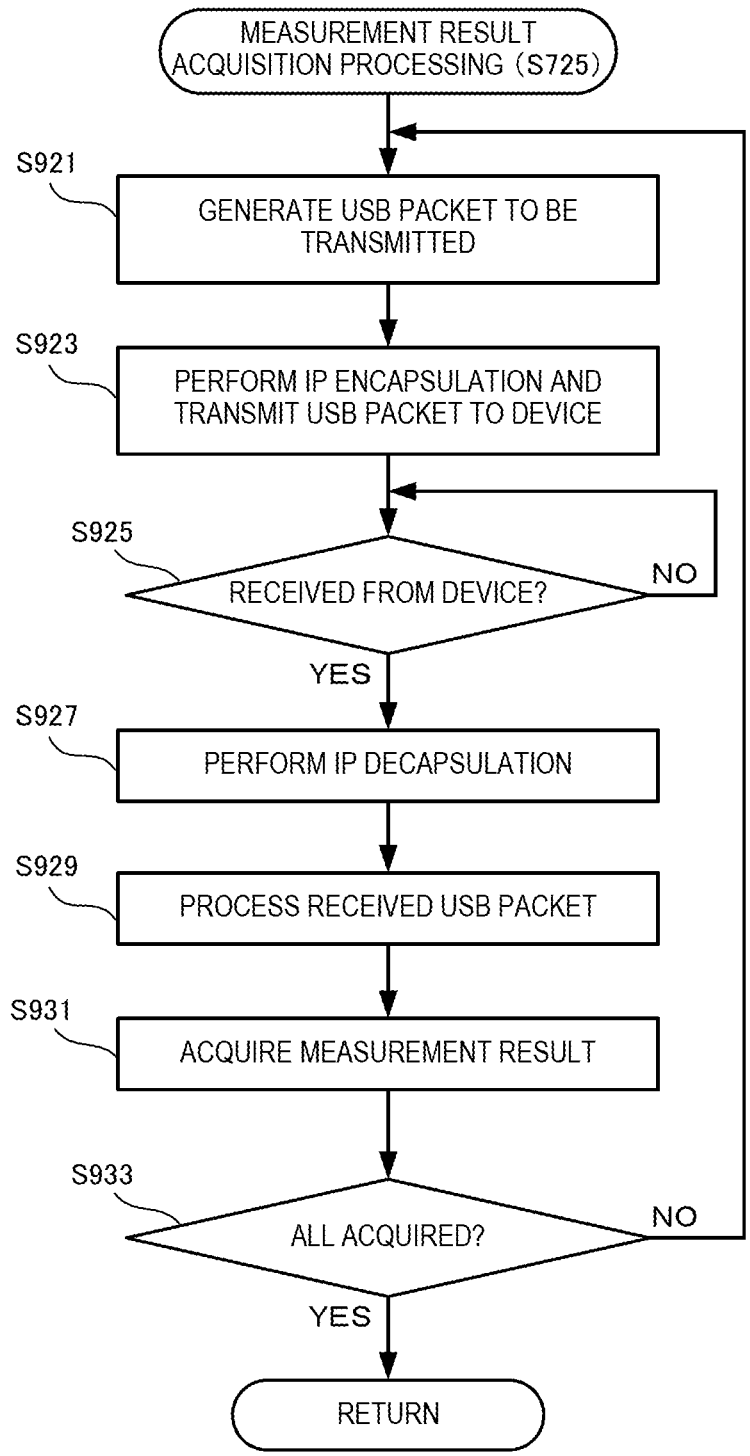
FIG. 9 is a flowchart showing the sequence of measurement result acquisition processing to be performed by the cloud server in the second embodiment of the present invention.

The processing (S725) of acquiring a measurement result by the cloud server 200 from the medical measurement device 261 or 262 will be explained in detail with reference to FIG. 9.

First, in step S921, the cloud server 200 generates a USB packet to be transmitted for obtaining a measurement result. Then, in step S923, the cloud server 200 performs IP encapsulation of the USB packet and transmits the USB packet to the medical measurement device 261 or 262.

In step S925, the cloud server 200 waits for reception of a USB packet from the medical measurement device 261 or 262. If the cloud server 200 receives a USB packet from the medical measurement device 261 or 262, it advances to step S927 to perform IP decapsulation. The cloud server 200 processes the received USB packet in step S929, and acquires a measurement result in step S931. The cloud server 200 repetitively performs the processes in steps S921 to S931 until all measurement results are acquired.

(Functional Arrangement of Smartphone)

Figure 10:
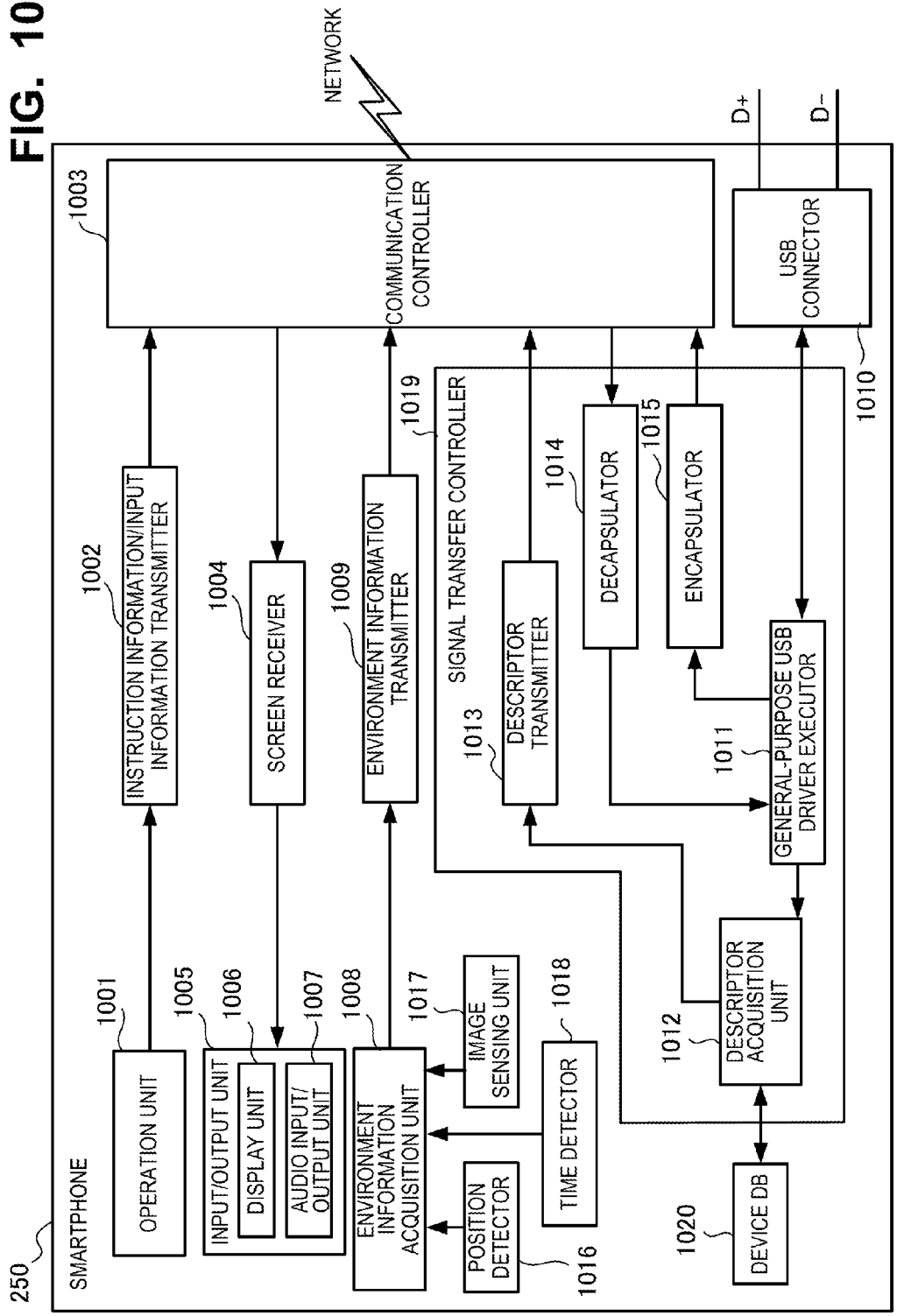
FIG. 10 is a block diagram showing the functional arrangement of the smartphone in the second embodiment of the present invention.

The functional arrangement of the smartphone 250 will be explained with reference to FIG. 10. The smartphone 250 includes an operation unit 1001 that accepts instructions and inputs from a user, and an instruction information/input information transmitter 1002 that transmits the accepted instruction information and input information. The smartphone 250 also includes a communication controller 1003, and controls exchange with a network.

The smartphone 250 also includes, as an input/output unit 1005, a display unit 1006 such as a display, and an audio input/output unit 1007 such as a microphone or a loudspeaker. A screen receiver 1004 receives audio information and image information via the communication controller 1003, and performs image output to the display unit 1006 and audio output from the audio input/output unit 1007.

Further, the smartphone 250 includes an environment information acquisition unit 1008, a position detector 1016, an image sensing unit 1017, and a time detector 1018. Position information detected by the position detector 1016 by using the GPS or the like, time information detected by the time detector 1018 such as a digital timepiece, image information such as the face of a measurement target person photographed using the image sensing unit 1017, and the like are sent as environment information to the environment information acquisition unit 1008. The environment information acquired by the environment information acquisition unit 1008 is transmitted to the cloud server 200 via an environment information transmitter 1009 and the communication controller 1003, and accumulated in the medical information database 210 as medical information together with measurement result information. Although an image photographed using the image sensing unit 1017 has been described, it is also possible to capture a video containing the face and voice of a measurement target person, link the captured video with measurement result information, and accumulate it in the medical information database 210.

Further, the smartphone 250 includes a USB connector 1010 and a general-purpose USB driver executor 1011. A descriptor acquisition unit 1012 is configured to be able to acquire a minimum descriptor from a connected USB device. The acquired descriptor is transferred to a descriptor transmitter 1013 and transmitted to the cloud server 200 via the communication controller 1003.

The smartphone 250 further includes a decapsulator 1014 and an encapsulator 1015. At the time of communication with the cloud server 200, the general-purpose USB driver executor 1011 causes the decapsulator 1014 and the encapsulator 1015 to perform decapsulation processing and encapsulation processing on USB packets that are exchanged with the cloud server 200.

The general-purpose USB driver executor 1011, the descriptor acquisition unit 1012, the descriptor transmitter 1013, the decapsulator 1014, and the encapsulator 1015 function as a signal transfer controller 1019 as a whole. That is, the signal transfer controller 1019 controls signal transfer between the medical measurement device 261 or 262 and the cloud server 200.

The smartphone 250 stores a device database 1020 representing the correspondence between a device descriptor, an interface descriptor, a vendor ID, and a product ID for a device whose device driver is installed in the local terminal. The device database 1020 has the same structure as that of the device database 623 shown in FIG. 7E.

When the medical measurement device 261 or 262 is connected, the smartphone 250 compares a device descriptor notified from the medical measurement device 261 or 262 with a device descriptor in the device database 1020. If the device descriptor notified from the medical measurement device 261 or 262 coincides with a device descriptor in the device database 1020, the smartphone 250 determines that the medical measurement device 261 or 262 is a device processable by the local terminal. If these device descriptors do not coincide with each other, the smartphone 250 determines that the medical measurement device 261 or 262 is a device unprocessable by the local terminal.

Note that a vendor ID and a product ID in a device descriptor notified from the medical measurement device 261 or 262 may be extracted and compared with a vendor ID and product ID in the device database. In this case, if a coincident vendor ID and product ID exist in the device database 1020, the smartphone 250 can determine that the medical measurement device is processable by the local terminal. To the contrary, if neither the vendor ID nor the product ID is coincident, the smartphone 250 can determine that the medical measurement device is unprocessable by the local terminal.

(Structure of Medical Information Database)

Figure 11:
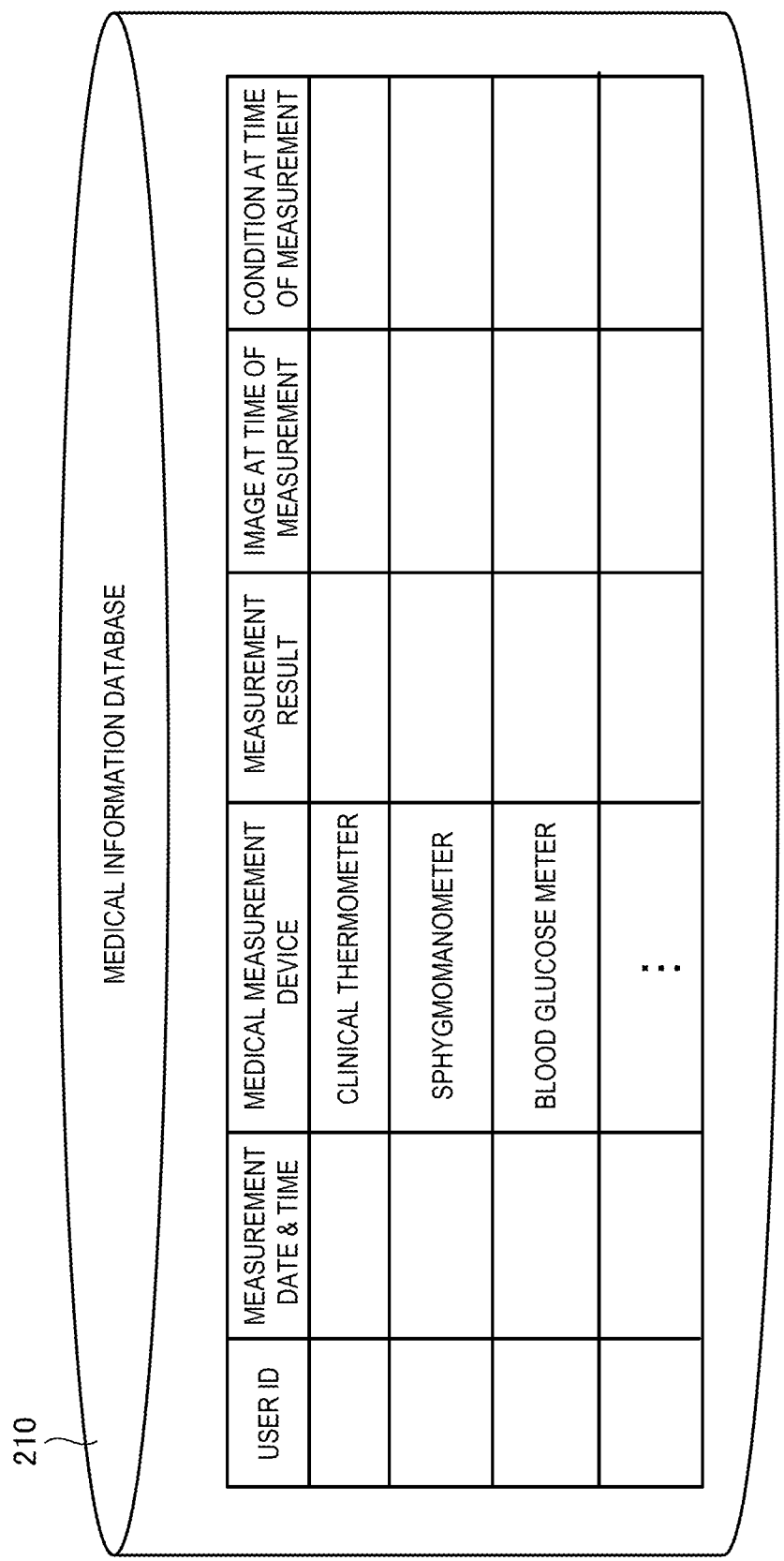
FIG. 11 is a view showing the structure of a medical information database in the second embodiment of the present invention.

FIG. 11 is a view showing an example of the medical information database 210. The medical information database 210 links the measurement date & time, the type of medical measurement device, and the measurement result to a user ID, and accumulates them. If necessary, the medical information database 210 also accumulates an image at the time of measurement, the explanation of a condition at the time of measurement, and the like in association with each other.

(Structure of Measurement Target Person Database)

FIG. 12 is a table showing an example of a measurement target person database accumulated and saved in the cloud server 200. The relevance with a registered user database in the cloud server 200 may be clarified to inform a user about services he can receive. In this database, pieces of information input by the user in advance, such as the user ID, user name, address, telephone number, mail address, age, sex, medical history, and chronic disease, are stored based on the individual number of the smartphone 250. Further, the family makeup of a main user and his personal information can be similarly stored. By generating such a database, not only the user of the smartphone 250 but also his family can receive the service of the cloud server 200 in the same way. The measurement target person database is also linked with the medical information database 210, and when a disease is specified based on information of the medical information database 210, the medical history portion of the measurement target person database is updated.

By the above-described arrangement and operation, the information processing system according to this embodiment can control the medical measurement device 261 or 262 that is connected to a smartphone and whose driver has not been preinstalled.

[Other Embodiments]

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The present invention is applicable to a system including a plurality of devices or a single apparatus. The present invention is also applicable even when a control program for implementing the functions of the embodiments is supplied to the system or apparatus directly or from a remote site. Hence, the present invention also incorporates the control program installed in a computer to implement the functions of the present invention on the computer, a medium storing the control program, and a WWW (World Wide Web) server that causes a user to download the control program.

This application claims the benefit of Japanese Patent Application No. 2012-123801 filed on May 30, 2012, which is hereby incorporated by reference herein in its entirety.

The invention claimed is:

1. An information processing apparatus comprising:
   an acquisition unit that, when a medical measurement device is connected to a portable communication terminal, acquires specifying information for specifying the medical measurement device via the portable communication terminal;
   a driver executer that executes a driver program corresponding to the specifying information without downloading a measuring program into the portable communication terminal;
   a first receiver that receives, via the portable communication terminal, measurement result information of a measurement target person measured by the medical measurement device;
   a second receiver that receives, from the portable communication terminal, measurement target person information for specifying the measurement target person measured by the medical measurement device; and
   an accumulator that accumulates the measurement target person information and the measurement result information in association with each other.

2. The information processing apparatus according to claim 1, further comprising a transmitter that transmits accumulated information to one of the portable communication terminal and a medical care worker communication terminal.

3. The information processing apparatus according to claim 2, wherein said transmitter applies statistical processing to the accumulated information, and transmits the accumulated information to one of the portable communication terminal and the medical care worker communication terminal.

4. The information processing apparatus according to claim 1, wherein said second receiver further receives, from the portable communication terminal, time information about time when the measurement result information was acquired from the medical measurement device.

5. The information processing apparatus according to claim 1, wherein the measurement target person is an individual registered in advance in association with an owner of the portable communication terminal, and
said first receiver receives, via the portable communication terminal, measurement result information about the individual measured by the medical measurement device.

6. The information processing apparatus according to claim 1, wherein said transmitter converts the information accumulated in said accumulator into display screen data that can be displayed on the portable communication terminal, and transmits the display screen data to the portable communication terminal.

7. The information processing apparatus according to claim 1, wherein a face of the measurement target person is photographed by using an image sensing unit incorporated in the portable communication terminal, and the photographed image is linked with the measurement result information and accumulated in said accumulator.

8. The information processing apparatus according to claim 1, wherein a video containing a face and voice of the measurement target person is captured by using an image sensing unit incorporated in the portable communication terminal, and the captured video is linked with the measurement result information and accumulated in said accumulator.

9. The information processing apparatus according to claim 1, wherein when transmitting the accumulated information to the medical care worker communication terminal, said transmitter performs time correction in consideration of a time difference based on location information of the medical care worker communication terminal.

10. An information processing method comprising:
    when a medical measurement device is connected to a portable communication terminal, acquiring specifying information for specifying the medical measurement device via the portable communication terminal;
    executing a driver program corresponding to the specifying information without downloading a measuring program into the portable communication terminal;
    receiving, via the portable communication terminal, measurement result information of a measurement target person measured by the medical measurement device;
    receiving, from the portable communication terminal, measurement target person information for specifying the measurement target person measured by the medical measurement device;
    accumulating the measurement target person information and the measurement result information in association with each other; and
    transmitting accumulated information to one of the portable communication terminal and a medical care worker communication terminal.

11. A non-transitory computer readable medium storing an information processing program for causing a computer to execute a method, comprising:
    when a medical measurement device is connected to a portable communication terminal, acquiring specifying information for specifying the medical measurement device via the portable communication terminal;
    executing a driver program corresponding to the specifying information without downloading a measuring program into the portable communication terminal;
    receiving, via the portable communication terminal, measurement result information of a measurement target person measured by the medical measurement device;

receiving, from the portable communication terminal, measurement target person information for specifying the measurement target person measured by the medical measurement device;

accumulating the measurement target person information and the measurement result information in association with each other; and transmitting accumulated information to one of the portable communication terminal and a medical care worker communication terminal.

12. A portable communication terminal comprising:

a determinator that determines, when a medical measurement device is connected via a communication interface, whether a local terminal can control the medical measurement device;

a request unit that, when said determinator determines that the local terminal cannot control the medical measurement device, accesses a server via a wireless communication network, and requests acquisition of measurement result information from the medical measurement device on the basis of specifying information that specifies the medical measurement device;

a signal transfer control unit that controls signal transfer between the medical measurement device and the server via the communication interface and the wireless communication network so as to be able to establish communication between the medical measurement device and the server and acquire, by the server, measurement result information measured by the medical measurement device as a result of the server executing a driver program corresponding to the specifying information without downloading a measuring program into the portable communication terminal; and a transmitter that transmits, to the server in association with each other, the measurement result information and measurement target person information for specifying a measurement target person.

13. A control method of a portable communication terminal, comprising:

determining, when a medical measurement device is connected via a communication interface, whether a local terminal can control the medical measurement device;

when the local terminal is determined in the determining not to be able to control the medical measurement device, accessing a server via a wireless communication network, and requesting acquisition of measurement result information from the medical measurement device on the basis of specifying information that specifies the medical measurement device;

controlling signal transfer between the medical measurement device and the server via the communication interface and the wireless communication network so as to be able to establish communication between the medical measurement device and the server and acquire, by the server, measurement result information measured by the medical measurement device as a result of the server executing a driver program corresponding to the specifying information without downloading a measuring program into the portable communication terminal; and transmitting, to the server in association with each other, the measurement result information and measurement target person information for specifying a measurement target person.

14. A non-transitory computer readable medium storing a control program of a portable communication terminal for causing a computer to execute a method, comprising:

determining, when a medical measurement device is connected via a communication interface, whether a local terminal can control the medical measurement device;

when the local terminal is determined in the determining not to be able to control the medical measurement device, accessing a server via a wireless communication network, and requesting acquisition of measurement result information from the medical measurement device on the basis of specifying information that specifies the medical measurement device;

controlling signal transfer between the medical measurement device and the server via the communication interface and the wireless communication network so as to be able to establish communication between the medical measurement device and the server and acquire, by the server, measurement result information measured by the medical measurement device as a result of the server executing a driver program corresponding to the specifying information without downloading a measuring program into the portable communication terminal; and transmitting, to the server in association with each other, the measurement result information and measurement target person information for specifying a measurement target person.

* * * * *